· US011045151B2

United States Patent
Jensen et al.

(10) Patent No.: US 11,045,151 B2
(45) Date of Patent: Jun. 29, 2021

(54) CONE-BEAM COMPUTED TOMOGRAPHY IMAGING DEVICES, SYSTEMS, AND METHODS

(71) Applicants: VARIAN MEDICAL SYSTEMS, INC., Palo Alto, CA (US); VARIAN MEDICAL SYSTEMS INTERNATIONAL AG, Zug (CH)

(72) Inventors: David Kirk Jensen, Sunnyvale, CA (US); Reto W. Filiberti, Steinhausen (CH); Markus Oelhafen, Rohr (CH); Aime Pascal Laurence Paysan, Basel (CH)

(73) Assignees: VARIAN MEDICAL SYSTEMS, INC., Palo Alto, CA (US); VARIAN MEDICAL SYSTEMS INTERNATIONAL AG, Steinhausen (CH)

( * ) Notice: Subject to any disclaimer, the term of this patent is extended or adjusted under 35 U.S.C. 154(b) by 878 days.

(21) Appl. No.: 15/036,669

(22) PCT Filed: Nov. 18, 2013

(86) PCT No.: PCT/US2013/070629
§ 371 (c)(1),
(2) Date: May 13, 2016

(87) PCT Pub. No.: WO2015/073048
PCT Pub. Date: May 21, 2015

(65) Prior Publication Data
US 2016/0278719 A1 Sep. 29, 2016

(51) Int. Cl.
*A61B 6/00* (2006.01)
*A61B 6/02* (2006.01)
*A61B 6/03* (2006.01)
*A61B 6/06* (2006.01)
*A61B 6/04* (2006.01)

(52) U.S. Cl.
CPC .............. *A61B 6/027* (2013.01); *A61B 6/032* (2013.01); *A61B 6/0487* (2020.08); *A61B 6/06* (2013.01); *A61B 6/4035* (2013.01); *A61B 6/4085* (2013.01); *A61B 6/4233* (2013.01); *A61B 6/4441* (2013.01); *A61B 6/4447* (2013.01); *A61B 6/5205* (2013.01); *A61B 6/025* (2013.01)

(58) Field of Classification Search
CPC ..................................................... A61B 6/032
See application file for complete search history.

(56) References Cited

U.S. PATENT DOCUMENTS

| 5,598,453 | A | * | 1/1997 | Baba | ....................... A61B 6/032 378/146 |
| 7,711,083 | B2 | * | 5/2010 | Heigl | ....................... A61B 6/032 378/20 |
| 7,826,592 | B2 | | 11/2010 | Jaffray et al. | |

(Continued)

OTHER PUBLICATIONS

International Search Report and Written Opinion dated Feb. 14, 2014, in International Application No. PCT/US2013/070629.
Bian et al., "Evaluation of Sparse-view Reconstruction from Flat-panel-detector Cone-beam CT," Phys. Med. Biol. Nov. 2010, 55 (22), pp. 6575-6599.

(Continued)

*Primary Examiner* — Dani Fox
(74) *Attorney, Agent, or Firm* — SGPatents PLLC

(57) ABSTRACT

Cone-beam computer tomography systems, devices, and methods for image acquisition of large target volumes using partial scans.

8 Claims, 14 Drawing Sheets

(56) References Cited

U.S. PATENT DOCUMENTS

| | | | |
|---|---|---|---|
| 8,116,430 | B1 | 2/2012 | Shapiro et al. |
| 8,121,245 | B2 | 2/2012 | Pan et al. |
| 8,135,111 | B2 | 3/2012 | Jaffray et al. |
| 8,254,518 | B2 | 8/2012 | Paidi et al. |
| 2004/0013225 | A1* | 1/2004 | Gregerson ............. A61B 6/032 378/19 |
| 2004/0264640 | A1 | 12/2004 | Myles |
| 2006/0285633 | A1* | 12/2006 | Sukovic ................ A61B 6/032 378/9 |
| 2009/0190714 | A1 | 7/2009 | Partain |
| 2011/0228906 | A1 | 9/2011 | Jaffray et al. |
| 2012/0020448 | A1 | 1/2012 | Khare et al. |
| 2012/0189102 | A1 | 7/2012 | Maurer |
| 2012/0243655 | A1* | 9/2012 | Ninomiya ............. A61B 6/027 378/8 |

OTHER PUBLICATIONS

Yang et al., "Circle Plus Partial Helical Scan Scheme for a Flat Panel Detector-Based Cone Beam Breast X-Ray CT," International Journal of Biomedical Imaging, vol. 2009, Article ID 637867.

Palm et al., "Absorbed dose and dose rate using the Varian OBI 1.3 and 1.4 CBCT system," Journal of Applied Clinical Medical Physics, 2010, vol. 11, No. 1, pp. 229240.

Siewerdsen et al., "Flat-Panel Cone-Beam CT: A Novel Imaging Technology for Image-Guided Procedures," *Proc. SPIE* 4319, Medical Imaging 2001: Visualization, Display, and Image-Guided Procedures, 435 (May 28, 2001); doi:10.1117/12.428085.

Abolaban, "On Board Cone Beam CT for Treatment Planning in Image Guided Radiotherapy," Department of Physics, Scholl of Electronic and Physical Sciences, University of Surrey, Guildford, GU2 7XH, Mar. 2011.

International Preliminary Report on Patentability dated May 24, 2016, in International Application No. PCT/US2013/070629.

\* cited by examiner

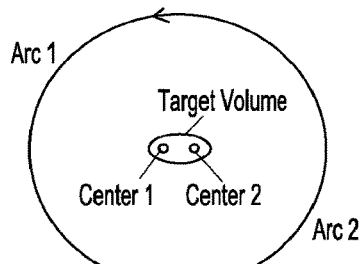
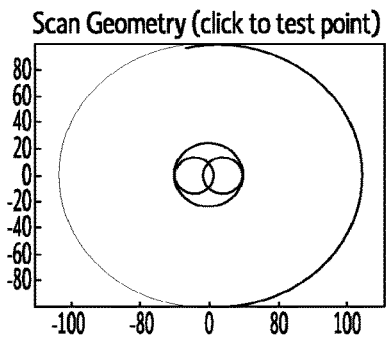
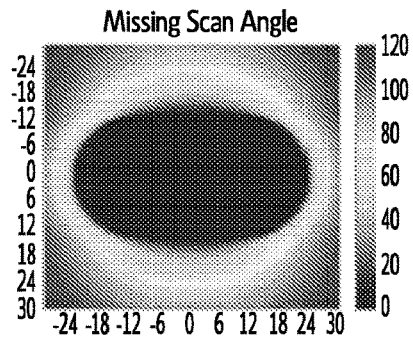
FIG. 11A          FIG. 11B          FIG. 11C
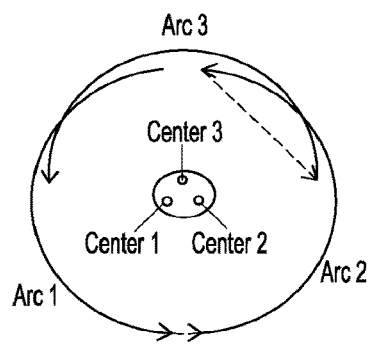
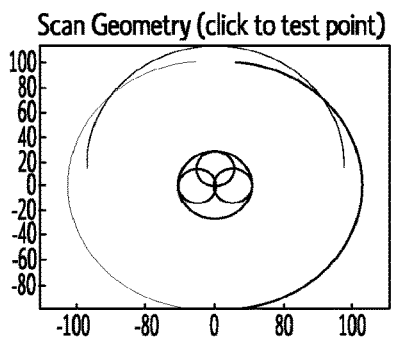
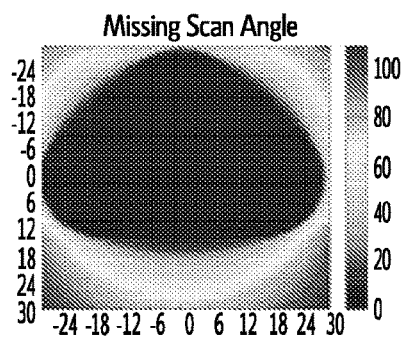
FIG. 14A          FIG. 14B          FIG. 14C
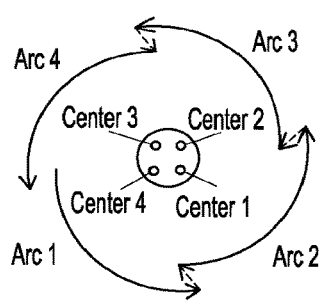
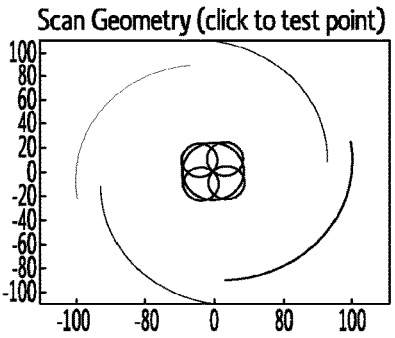
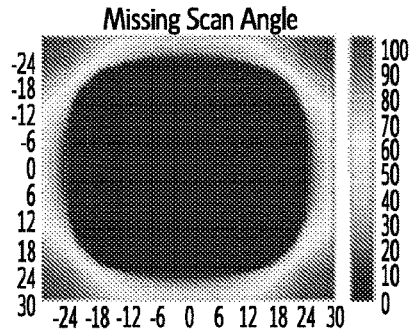
FIG. 17A          FIG. 17B          FIG. 17C

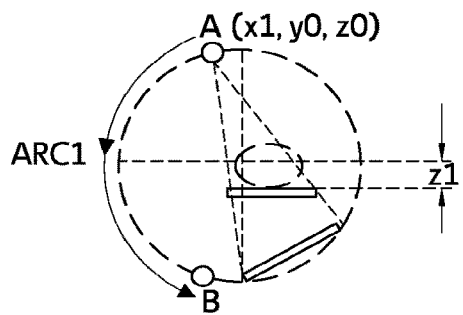
FIG. 13A
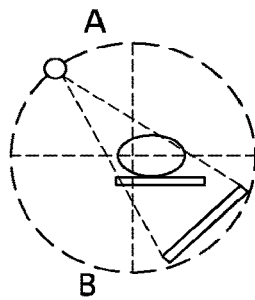
FIG. 13B
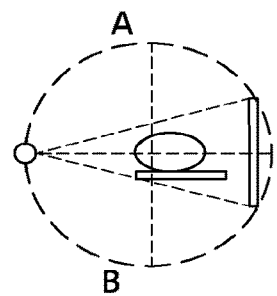
FIG. 13C
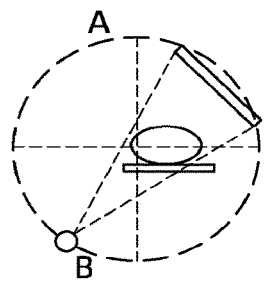
FIG. 13D
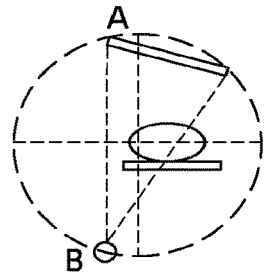
FIG. 13E
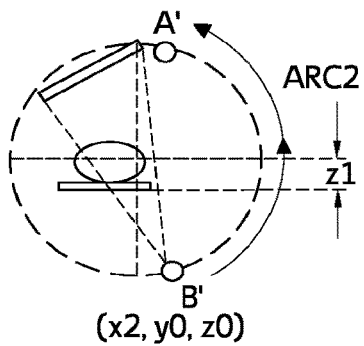
FIG. 13'A
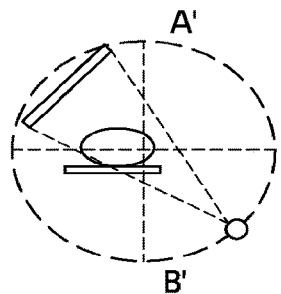
FIG. 13'B
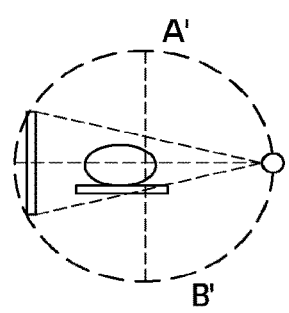
FIG. 13'C
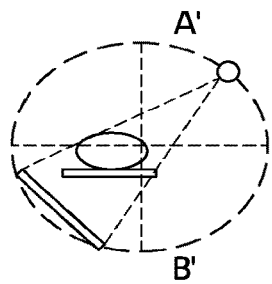
FIG. 13'D
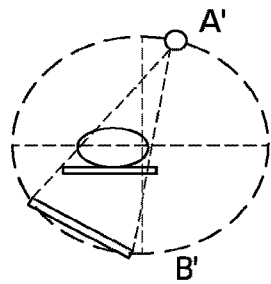
FIG. 13'E

CONE-BEAM COMPUTED TOMOGRAPHY IMAGING DEVICES, SYSTEMS, AND METHODS

FIELD

The present disclosure relates generally to radiation therapy systems, devices, and methods, and more particularly to cone-beam computed tomography systems, devices, and methods for imaging larger anatomies with reduced field sizes while keeping the source data coverage for the reconstruction of the computed tomography (CT) volume complete.

BACKGROUND

Radiotherapy involves delivering a prescribed radiation dose to a specific geometrically defined target or target volume. Typically this treatment is delivered to a patient in one or more therapy sessions. While radiotherapy has proven successful in managing various types and stages of cancer, the potential exists for increased tumor control through increased dose. Unfortunately, delivery of increased dose is limited by the presence of adjacent normal/healthy structures (tissues) and the precision of radiation beam delivery.

In order to reduce the dosage to normal/healthy structures, the location of the target volume relative to the radiation therapy source must be known precisely in each treatment session in order to accurately deliver the radiation dose while minimizing complications in normal/healthy structures/tissues. Traditionally, a radiation therapy treatment plan is formed based on the location and orientation of the lesion and surrounding structures in an initial computerized tomography (CT) or magnetic resonance image.

Because computed tomography (CT) uses the X-ray with photon energy ranging from 80 to 140 kVp with multiple projections, the radiation dose to the patient is a concern. A general 360 degree CT imaging results in approximately 1000 projections and total tube current time of 200 mAs per rotation with the effective photon energy of 60-70 keV. As a result, the average effective dose from CT imaging is about 100-250 times higher than that of a regular chest X-ray imaging.

A centrally located detector/imager cone-beam CT (CBCT) system (i.e., the detector/imager matrix nearly centered on the axis of the X-ray beam) allows for acquiring a larger imaging area with fewer number of projections, while reducing the scan duration, and thus the dose. A centrally located detector/imager CBCT system however, has a limited field of view (FOV) (the FOV is typically constrained to smaller anatomy (e.g., ~25 and ~40 cm for a typical "head" and "body", respectively). Imaging an object at a smaller field of view introduces lateral truncation effects. Lateral truncation of the object in projection views can be an issue because it can cause significant reconstruction artifacts, especially if high contrast structures are presented inconsistently between views.

The FOV can be increased using an offset geometry (i.e., imager offset from the axis of the X-ray beam), but this technique requires acquisition of projections across 360 degrees, which increases acquisition time and radiation dose. The offset imager geometry also increases the complexity, weight, and cost of the imaging system. Further, even with the advantage of a larger field of view for the offset imager geometry, the field of view is still limited to up to 50 cm.

For a larger anatomy (i.e., larger than 50 cm in diameter), a larger field of view is necessary. A larger FOV can be obtained by using a kilovoltage (kV) X-rays source having a field size of approximately 50 cm and more. A larger FOV, however, increases acquisition time, and radiation dose. It also introduces X-ray scatter artifacts into the reconstructed image.

A reduced field size, such as that obtained using a megavoltage (MV) X-ray source with field sizes on the order of ~40 cm maximum or a (kV) X-rays source with field sizes much less than the currently used 50 cm, is advantageous over larger field sizes because it allows for an increase in dose-rate at the center area of the field. It can also decrease X-ray scatter and can reduce the cost of the machine. However, a reduced field size limits the size of the object that can be imaged, which then increases the lateral truncation effect of the object in projection views. For example, the treatment field size is on the order of ~40 cm maximum at the isocenter for a MV X-ray source, which means that with a half-fan image acquisition mode, image reconstruction is limited to objects up to ~39.2 cm in diameter. For smaller MV fields, on the order of about 35 cm, for example, the image reconstruction is limited to even smaller object diameters (about 34.5 cm).

An exemplary scanning diameter and imaging volume obtained using a conventional scanning trajectory is illustrated in FIGS. 5A-C. The X-ray source is moved in a 180 degree+fan angle arc segment (ARC1) from first position A to a second position B around a target volume positioned between the X-ray source and the detector. The scanning diameter and scanning volume obtained is shown in FIG. 6, and the imaged target volume is as shown in FIG. 7. Because of the reduced scanning diameter and imaging volume, imaging data is missing for the outer areas of the target volume. Such missing data can introduce artifacts in the reconstructed 3D image.

Therefore, although using MV fields or kV fields of much less than 50 cm field sizes are beneficial because it reduces X-ray scatter, the imaged object using a conventional scanning and imaging method is limited to at most ~40 cm in diameter, which limits the data source for the reconstruction of the CT volume.

There is a need therefore, for a centered geometry CBCT imaging device, system, and method that overcomes the field size limitation and allows for imaging of a larger anatomy (i.e., over 50 cm in diameter), as well as smaller anatomy (smaller than 50 cm in diameter) with reduced field sizes (i.e., with megavoltage (MV) fields between 25 cm and 40 cm maximum, or kilovoltage (kV) fields which are significantly smaller than the currently used 50 cm) while keeping the source data coverage for the reconstruction of the CT volume complete.

SUMMARY

The present disclosure describes cone-beam computed tomography (CBCT) imaging devices, systems, and methods for imaging a larger anatomy (i.e., over 50 cm in diameter) with reduced field sizes (i.e., with megavoltage (MV) fields between 25 cm and 40 cm maximum, or kilovoltage (kV) fields which are smaller than the currently used 50 cm), while keeping the source data coverage for the reconstruction of the CT volume complete.

In embodiments, this is accomplished by using image acquisition trajectories/modes by which imaging diameters, imaging volumes, and imaging data are increased.

The present disclosure describes CBCT imaging devices, systems, and methods to increase the scanning diameter and the imaging volume. In order to increase the scanning diameter and the imaging volume, projection images are acquired by rotating the gantry around the rotation axis to allow the X-ray source to move around the target in a plurality of scanning trajectories as well as moving the target in planes orthogonal to the rotation axis of the gantry to different locations. Moving the target to different locations leads to a virtual movement of the rotation center relative to the imaging volume and thus to the increase of the scanning diameter. Moving the target to different locations can be accomplished by moving the treatment couch along planes that are orthogonal to the rotation axis of the gantry. The present disclosure describes CBCT imaging devices, systems, and methods to increase the imaging volume by moving the treatment couch along a lateral and/or vertical axis to different locations and scanning the patient at the respective couch positions by rotating the gantry around the patient in a scanning trajectory.

Embodiments of the CBCT devices, systems, and methods described herein allow for volume reconstruction using a fixed, centrally located detector/imager configuration without introducing imaging artifacts.

Embodiments of the CBCT devices, systems, and methods described herein allow for volume reconstruction using a fixed, off center located detector/imager configuration without introducing imaging artifacts.

Embodiments of the CBCT devices, systems, and methods described herein allow for volume reconstruction using a movable detector/imager configuration without introducing imaging artifacts.

Embodiments described herein include image acquisition trajectories/modes by which imaging volumes and imaging data are increased while reducing X-ray scatter and acquisition time.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features.

FIGS. 11A-11B illustrate the scan trajectory and the target volume obtained using the image acquisition mode of FIGS. 9A-10E.

FIG. 11C illustrates a central slice of the reconstructed volume obtained using the scan trajectory of FIGS. 11A-11B.

FIGS. 13A-13H and 13'A-13'E illustrate an image acquisition mode according to one or more embodiments of the disclosed subject matter.

FIGS. 14A-14B illustrate the scan trajectory and the target volume obtained using the image acquisition mode of FIGS. 13A-13C.

FIG. 14C illustrates a central slice of the reconstructed volume obtained using the scan trajectory of FIGS. 14A-14B.

FIG. 17A-17B illustrate the scan trajectory and the target volume obtained using the image acquisition mode of FIGS. 16A-16C.

FIG. 17C illustrates a central slice of the reconstructed volume obtained using the scan trajectory of FIGS. 17A-17B.

DETAILED DESCRIPTION

A cone-beam computed tomography (CBCT) system reconstructs three-dimensional (3-D) images from a plurality of two-dimensional (2-D) projection images acquired at various angles about a subject. The method by which the 3-D image is reconstructed from the 2-D projections is distinct from the method employed in conventional computerized tomography (CT) systems. In conventional CT systems, one or more 2-D slices are reconstructed from one-dimensional (1-D) projections of the patient, and these slices are stacked to from a 3-D image of the patient. In CBCT, a full 3-D image is reconstructed from a plurality of 2-D projections.

CBCT offers a number of advantageous characteristics, including formation of a 3-D image of the patient from a single rotation about the patient, spatial resolution that is largely isotropic, and greater flexibility in the imaging geometry. CBCT can also be employed on numerous platforms, such as, on a rotating CT gantry, a rotating medical linear accelerator gantry, or an isocentric C-arm platform. Each of these platforms incorporates an X-ray source (X-ray tube or MV target) and a detector/flat-panel imager, from which multiple 2-D projections are acquired as a function of position about an object. The projections are then used to reconstruct a full 3-D image of the object using various volume reconstruction algorithms.

In operation, an X-ray source and an opposing detector/imager are manipulated to generate X-ray images of the patient interposed between the source and the detector. CT scan images of the target volume are generated while the treatment couch is moved to different positions within planes which are orthogonal to the rotation axis of the gantry and the X-ray source is moved around the patient. By moving the treatment couch as well as the gantry (and thus the X-ray source) to acquire the projection images, the scan diameter and thus the imaging volume can be increased.

The cone-beam computed tomography image data can then be used to generate a three-dimensional representation of the patient anatomy and the target volume, for visualization of soft and bony tissues with excellent spatial resolution. The image data may further be used to generate a treatment plan to tailor a dose of therapeutic radiation to the target volume.

A. Imaging Platforms

The novel CBCT image acquisition modes can be incorporated into different imaging platforms, including, but not limited to, ring gantry, on-board (OBI or On Board Imaging system on a C-arm Linac), and C-arm imaging platforms, for example.

Figure 1:
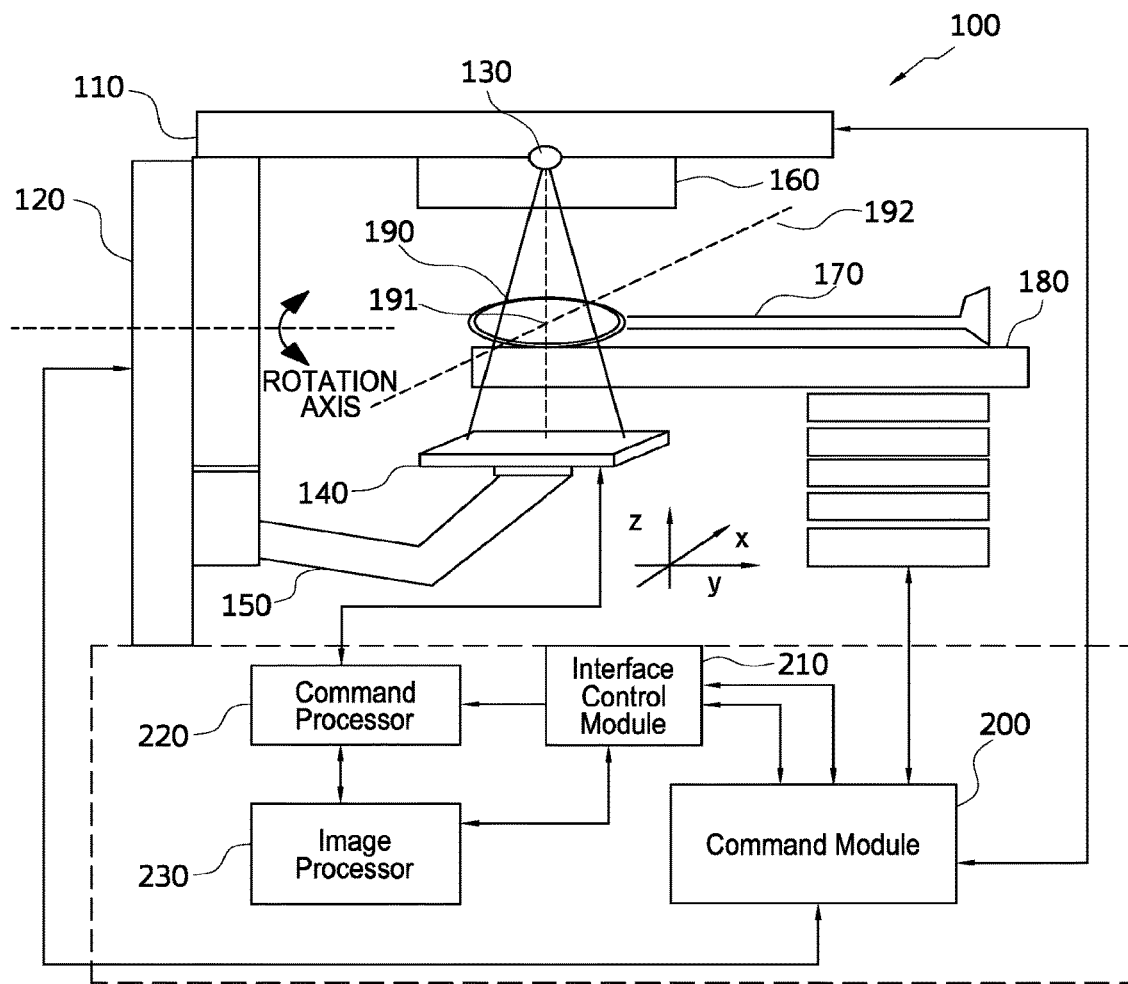
FIG. 1 is a perspective view of an imaging system employing a cone-beam computed tomographic image acquisition mode, according to one or more embodiments of the disclosed subject matter.

In an embodiment, a C-arm radiation therapy system 100 is disclosed employing CBCT as illustrated in FIG. 1. The system 100 includes a rotatable gantry 110 pivotably attached to a drive stand 120. A cone-beam computed tomography (CBCT) radiation source 130 and an imaging device 140, such as a flat-panel imager, oppose each other and are attached to the rotatable gantry 110. The flat-panel imager 140 is centrally positioned, meaning, the flat-panel-imager matrix is positioned orthogonal to the central beam at a fixed distance from the X-ray source (i.e., at 150 cm, for example). The flat-panel imager matrix is also substantially centered on the axis of the X-ray beam. The flat-panel imager 140 may be fixedly attached to the gantry in any manner, including via extendable and retractable housing 150. The cone-beam CT radiation source 130 may be a megavoltage (MV) radiation source, generally in the 4-25 MV energy range and having a field size on the order of between 25 cm and 40 cm maximum, or a kilovoltage (kV) radiation source having a field size which is smaller than 50 cm, for example. The kV source can be a pulsed or a continuous kV source. The system 100 may also include a linear accelerator 160 and a collimator (not shown) for collimating and shaping the radiation field that is directed onto the patient 170 supported on a treatment couch (table) 180 in a given treatment position.

The treatment couch 180 is positioned adjacent to the gantry 110 to place the patient 170 and the target volume 190 within the range of operation for the X-ray source 130 and the imager 140. The treatment couch 180 may be connected to the rotatable gantry 110 via a communications network and is capable of translating in multiple planes along the X, Y and Z axis, and angulation for positioning and repositioning the patient 170 and the target volume 190. The treatment couch 180 can be translated in the horizontal (i.e., along the Y axis), vertical (i.e., along the Z axis) and lateral (i.e., along the X axis) planes, and be coupled to an automated patient positioning system capable of manipulating the patient with three or more degrees of freedom (e.g., three orthogonal translations plus one or more rotations). The three orthogonal translations can include one parallel to the rotation axis (i.e., along the Y axis), and two orthogonal to the rotation axis (i.e., along the X and Z axis). The treatment couch can be a six-degrees-of-freedom (6DoF) treatment couch, for example.

Associated with this system is an imaginary plane, termed the transverse isocentric plane that is orthogonal to the rotation axis, which extends along the Y axis, and passes through an isocenter 191. The isocenter 191 is a fixed physical point in a treatment room. A treatment center is a point within the target volume 190 of the patient defined by a physician during treatment planning, normally based on a pretreatment image reference frame. For isocentric treatment, the treatment center is aligned with the isocenter 191 during a set up procedure.

The gantry 110 can rotate about the rotation axis to place the radiation source 130 and imager 140 at any position within 360 degrees around the target volume 190 to generate CT scan image data. The radiation source 130 can emit a divergent beam of X-rays along a beam axis. The beam is emitted toward the isocenter 191. Due to the divergence of the beam and the shaping of the beam by beam-shaping devices (not shown), the beam delivers the radiation to a volume of object rather than only to the isocenter 191. The flat panel imager 140 is configured to receive the X-rays that passed through the target volume 190 and to generate images based on the received X-rays. The CBCT scan image data can then be used to generate a three-dimensional representation of the patient 170 anatomy and the target volume 190. The image data may be further used to generate a treatment plan to tailor a dose of therapeutic radiation to the target volume 190.

To control the quality of the images, two types of filters, namely, full and half Bow-tie filters can be added. The main function of the filters is to reduce skin dose, reduce X-ray scatter, which results in improved image quality, reduce the amount of charge trapped in the detector, and to allow higher magnitude X-ray techniques to be used without saturating the detector.

The detector/imager 140 can include a large flat-panel imager, such as an amorphous silicon (a-Si) imager, having up to 43 cm in lateral dimension and ~30-43 cm in longitudinal dimension, for example. The imager 140 can operate at a frame-rate of 7.5 fps in full resolution mode and at a frame rate of 30 fps in 2×2 binned mode, for example. Any other applicable detectors or imagers may be used, however. The imager 140 may be coupled to signal processing circuitry comprising a preamplifier stage to improve contrast resolution and dynamic range.

The system 100 can also include a system controller 1000 comprising a processing circuitry, a detector controller, a couch position controller, and a radiation source controller, each programmed and configured to achieve one or more of the functionalities described herein. For example, the system controller may include a control module 200 for controlling the accelerator 160, the gantry angle, the X-ray beam intensity, the collimator (not shown), as well as the movement of the treatment couch 180, a command processor module 220 for controlling the imager 140 and for transferring image data between the imager 140 and an image processor 230, an interface control module 210 for gate and synchronization control between the control module 200, the command processor 220, and an image processor 230. The command processor module 220 is configured to process the digital images from the imager 140, and to provide interfaces to other system components. The command processor module 220 may also include a microcontroller-based, single board computer, running a real-time operating system with acquisition, control, and interface software. It may also include high speed digital video interface card, a dedicated image processor card, and a parallel output to transmit the image data to an external image processor and display.

Figure 2:
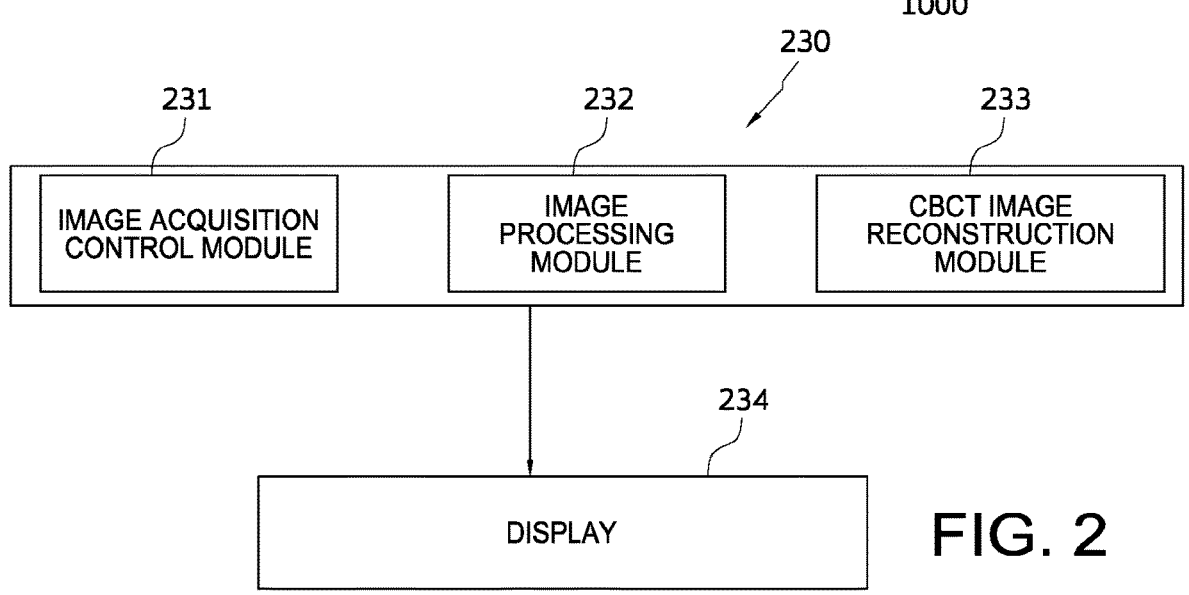
FIG. 2 illustrates components of an image processor, according to one or more embodiments of the disclosed subject matter.

The image processor 230 is configured to control the synchronized movement of the gantry 110, the radiation source 130, the imager 140, and the treatment couch 180. The image processor 230 may also include an image acquisition control module 231 to control timing of the exposure of the patient 170 to X-rays, image data readout from the imager 140, and rotation of the gantry, an image processing module 232 including software and hardware components to process the projection images by applying gain and offset corrections, and a CBCT image reconstruction module 233 by which a volumetric computerized tomography data set is reconstructed from the projections using a filtered back-projection or iterative algorithm, for example. These components are shown in FIG. 2. The system 100 may also include a power supply module, interconnecting cables, and drive and readout circuits followed by digital conversion and transmission capabilities.

The cone-beam scanning procedure includes a repeated sequence of radiographic exposure, array readout, object, treatment couch, gantry, and imaging module (source/detector) movement, as disclosed in detail below. The timing of this scanning procedure is driven by the frame clock of the flat panel imager 140.

Projection image acquisition is done by moving the treatment couch 180 laterally (along the X-axis), and/or vertically (along the Z-axis), and/or horizontally (along the Y-axis) and rotating the gantry 110 around the target volume 190. The rotation of the gantry 110 causes the radiation source 130 and the flat-panel imager 140 to rotate together around the isocenter 191, such that the isocenter 191 remains located between the radiation source 130 and the imaging device 140 during rotation. Moving the treatment couch 180 laterally, and/or vertically, and/or horizontally, or in a combination of lateral/vertical/horizontal movements, moves the target volume 190 from a first position to different positions which are shifted relative to the original position. This movement of the target volume leads to a virtual movement of the rotation center relative to the target volume and an increase in the covered scan diameter and thus the imaging volume, as shown in FIGS. 11A-11C, 14A-14C, and 17A-17C, discussed in detail below.

The captured cone-beam CT image projection data may be delivered to the command processor module 230 or be delivered and stored to another computer that can be connected to the command processor module 230 via a communication network or directly to another computer input or processing module. The cone-beam CT image projection data may also be transferred to a cone-beam CT reconstruction computer that includes software designed to achieve rapid cone-beam CT image generation. The computer can merge or reconstruct the image data into a three-dimensional representation of the patient and target volume.

In an embodiment, cone-beam CT reconstruction software can allow for full-cone and partial-cone input data that can produce cone-beam CT images at a specific source-to-imager distance. The cone-beam reconstruction software may also transform the cone-beam CT projection data into volumetric CT image data. The volumetric CT image data may include full-fan and/or partial cone image data to reconstruct head size and body size volumes of more than 50 cm in diameter.

The gantry structure 110 can also be configured to be coupled to and/or integrated with a computer system using one or more busses, networks, or other communication systems including wired or wireless communication systems to implement the imaging and reconstruction methods described herein. Methods of the cone-beam computer tomographic system may be implemented in machine readable code (i.e., software or computer program product) and performed on computer systems.

System 100 may incorporate less or more elements that those shown. In addition embodiments are not limited to the devices shown in these figures.

The image acquisition trajectories/modes used to generate image projections using this system is described in detail below under the heading "Image Acquisition Modes".

Figure 3:
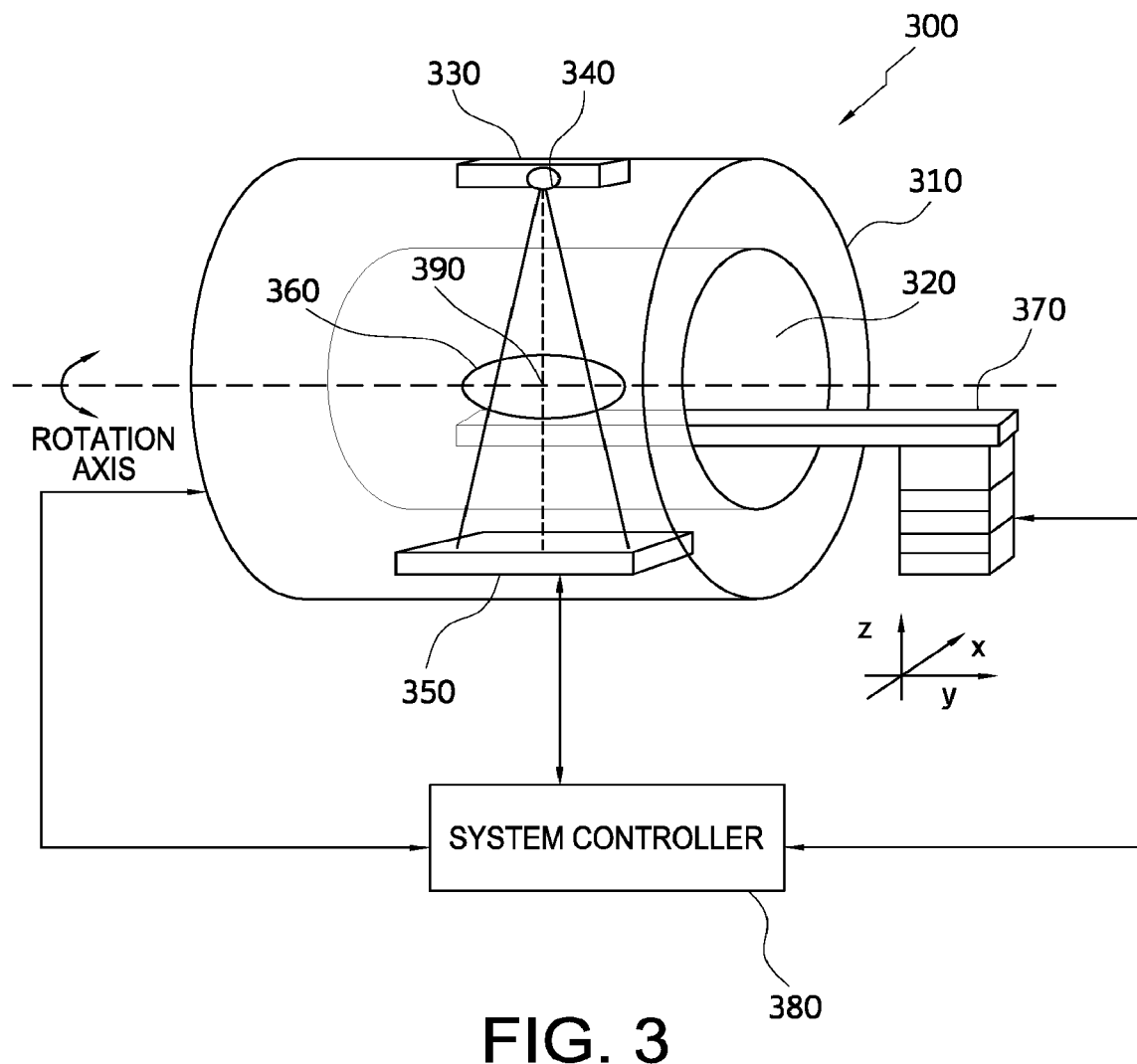
FIG. 3 is a perspective view of an imaging system employing a cone-beam computed tomographic image acquisition mode, according to one or more embodiments of the disclosed subject matter.

In an alternative embodiment, the CBCT is part of an image-guided radiation treatment (IGRT) system 300 including a ring gantry 310, as shown in FIG. 3. The ring gantry 310 has a central opening 320, a radiation treatment head 330 coupled to the ring gantry 310 and rotatable around the central opening 320 in at least a 180 degree arc. In one embodiment, the radiation treatment head 330 is rotatable around the central opening in full 360 degree arc. The radiation treatment head 330 includes a beam-emitting source 340 for emitting a radiation beam during calibration, acquisition of projection images, and/or treatment. In some embodiments, the beam-emitting source 340 is a megavoltage (MV) radiation source, generally in the 4-25 MV energy range and having a field size on the order of between 25 cm and 40 cm maximum, or a kilovoltage (kV) radiation source having a field size which is smaller than 50 cm, for example. The kV source can be a pulsed or a continuous kV source. The treatment head 330 may also include a beam-shielding device or collimator (not shown) for shaping the beam and for shielding sensitive surfaces from the beam. The collimator may be rotated and various elements of the collimator may be positioned according to a treatment plan. The collimator thus may control a cross-sectional shape of the beam.

Imaging is provided by an imaging system 350 including an imaging detector that can be fixably mounted to the ring gantry 310 to be rotatable in unison with the radiation treatment head 330 around the central opening 320. The MV X-ray source 340 can selectively apply high energy X-rays to a target volume 360 of a patient positioned on the treatment couch 370. The source 340 applies radiation under the control of a system controller 380. The system controller 380 can comprise a processing circuitry, a detector controller, a couch position controller, and a radiation source controller, each programmed and configured to achieve one or more of the functionalities described herein. The system controller 380 may include the components as described in detail above with regards to the system controller 1000.

The radiation source 340 can selectively emit X-rays under the control of the radiation controller 380, and the X-rays that have propagated from the X-ray source through the target volume 360 can be captured by an imaging detector, such as, a flat-panel imager 350. The flat-panel imager 350 is centrally positioned, meaning, the flat-panel-imager matrix is substantially centered on the axis of the X-ray beam. A couch position controller can be used to position the treatment couch 370. The treatment couch 370 can be moved in lateral (along the X-axis), horizontal (along the Y-axis), and vertical planes (along the Z-axis). The treatment couch 370 can be a six-degrees-of-freedom (6DoF) treatment couch, for example.

The treatment couch 370 may be connected to the rotatable gantry 310 via a communications network and is capable of translating in multiple planes along the X, Y and Z axis, and angulation for positioning and repositioning the patient and the target volume 360. The treatment couch 370 can be translated in the horizontal (i.e., along the Y axis), vertical (i.e., along the Z axis) and lateral (i.e., along the X axis) planes, and be coupled to an automated patient positioning system capable of manipulating the patient with three or more degrees of freedom (e.g., three orthogonal translations plus one or more rotations). The three orthogonal translations can include one parallel to the rotation axis (i.e., along the Y axis), and two orthogonal to the rotation axis (i.e., along the X and Z axis).

The gantry 310 can rotate about a rotation axis to place the radiation source 340 and imager 350 at any position within 360 degrees around the target volume 390 to generate CT scan image data.

The radiation source 340 can emit a divergent beam of X-rays along a beam axis. The beam is emitted toward the isocenter 390. Due to the divergence of the beam and the shaping of the beam by beam-shaping devices (not shown), the beam delivers the radiation to a volume 360 of object rather than only to the isocenter 390. The flat panel imager 350 is configured to receive the X-rays that passed through the target volume 360 and to generate images based on the received X-rays. The CBCT scan image data can then be used to generate a three-dimensional representation of the patient anatomy and the target volume 360. The image data may be further used to generate a treatment plan to tailor a dose of therapeutic radiation to the target volume 360.

To control the quality of the images, two types of filters, namely, full and half Bow-tie filters can be added. The main function of the filters is to reduce skin dose, reduce X-ray scatter, which results in improved image quality, reduce the amount of charge trapped in the detector, and to allow higher magnitude X-ray techniques to be used without saturating the detector.

The detector/imager 350 can include a large flat-panel imager, such as an amorphous silicon (a-Si) imager, having up to 43 cm in lateral dimension and ~30-43 cm in longitudinal dimension, for example. However, any other type of detectors and imagers can be used. The imager 350 may be coupled to signal processing circuitry comprising a preamplifier stage to improve contrast resolution and dynamic range.

In one embodiment, the ring gantry structure 300 may comprise a frame (not shown) within which is disposed the ring gantry 310, and mounted to the ring gantry 310 is the radiation treatment head 330, such as a linear accelerator or a compact proton source, for example, which can include thereon a collimator, such as, a multileaf collimator and which provides the radiation beam.

In either of the ring gantry embodiments (with or without the frame), the ring gantry 310 and radiation treatment head 330 are configured such that the radiation treatment head 310 is rotatable around the longitudinally oriented central axis passing through the isocenter 390. Any mechanism, as would be apparent to one of ordinary skill in this art, can be used to achieve such a rotating functionality, including a mechanism in which the ring gantry 310 is fixed while the radiation treatment head slides or rolls therearound, and/or mechanisms where the entire ring gantry 310 rotates and the radiation treatment head 330 is affixed to a single point thereon, and/or various combinations thereof. In all scenarios, "gantry angle" represents the angular disposition of the radiation treatment head 330 relative to the central longitudinal axis (rotation axis) as viewed axially from an end of the device. It is to be appreciated that any of the variety of different mechanism support schemes that allow such a variation of the gantry angle can be used.

The ring gantry 310 and the radiation treatment head 330 are configured and dimensioned so as to allow the central opening 320 to be sufficient to allow a patient to be positioned there through. A shielding or cover structure (not shown) could be provided to line the boundary of the central bore as well as to cover the sides of the ring gantry 310. The shielding structure could be of a material that is substantially transparent to the therapeutic and imaging radiation, and optionally can be visible opaque as well.

The cone-beam scanning procedure includes a repeated sequence of radiographic exposure, array readout, object, and/or radiation treatment head 330 movement, as disclosed in detail below. The timing of this scanning procedure is driven by the frame clock of the imaging system which is reading the flat panel imager 350. Projection image acquisition is done by moving the treatment couch 370 laterally (along the X-axis) and/or vertically (along the Z-axis), and rotating the gantry 310 around the target volume 360. The rotation of the gantry 310 causes the radiation treatment head 330 and the flat-panel imager 140 to rotate together around the isocenter 390, such that the isocenter 390 remains located between the radiation treatment head 330 and the imaging device 350 during rotation. Moving the treatment couch 370 laterally, and/or vertically, and/or horizontally, or in a combination of lateral/vertical/horizontal movements, moves the target volume 360 from a first position to different positions which are shifted relative to the original position. This movement of the target volume leads to a virtual movement of the rotation center relative to the target volume and an increase in the covered scan diameter and thus the imaging volume, as shown in FIGS. 11A-11C, 14A-14C, and 17A-17C, discussed in detail below.

The captured cone-beam CT image projection data may be delivered to the system controller 380 including the command processor module such as the command processor module 230 or be delivered and stored to another computer that can be connected to the command processor module via a communication network. The cone-beam CT image projection data may also be transferred to a cone-beam CT reconstruction computer that includes software designed to achieve rapid cone-beam CT image generation. The computer can merge or reconstruct the image data into a three-dimensional representation of the patient and target volume.

In an embodiment, cone-beam CT reconstruction software can allow for full-cone and partial-cone input data that can produce cone-beam CT images at a specific source-to-imager distance. The cone-beam reconstruction software may also transform the cone-beam CT projection data into volumetric CT image data. The volumetric CT image data may include full-fan and/or partial cone image data to reconstruct head size and body size volumes.

Beam shaping may also be employed along with intensity modulation by directing the X-ray beam through a dynamic multileaf collimator. The multileaf collimator may include a series of stacked metal shims having a center of shim pairs where each shim of the pairs may be individually moved to create a shaped opening capable of shaping the beam. To be effective, the radiation field should be large enough to radiate the entire tumor while at the same time minimize radiating healthy tissue. The collimator may be dynamic in that the shims can rapidly move to reshape the beam, which results in blocking the therapeutic beam from striking certain areas of the target volume based on the treatment plan. This results in different areas of the tumor receiving different amounts of radiation over the time that a radiation dose is applied.

The gantry structure 310 can also be configured to be coupled to and/or integrated with a computer system using one or more busses, networks, or other communication systems including wired or wireless communication systems to implement the imaging and reconstruction methods described herein. Methods of the cone-beam computer tomographic system may be implemented in machine readable code (i.e., software or computer program product) and performed on computer systems.

System 300 may incorporate less or more elements that those shown. In addition embodiments are not limited to the devices shown in these figures.

The image acquisition trajectories/modes used to generate image projections using this system is described in detail below under the heading "Image Acquisition Modes".

Figure 4:
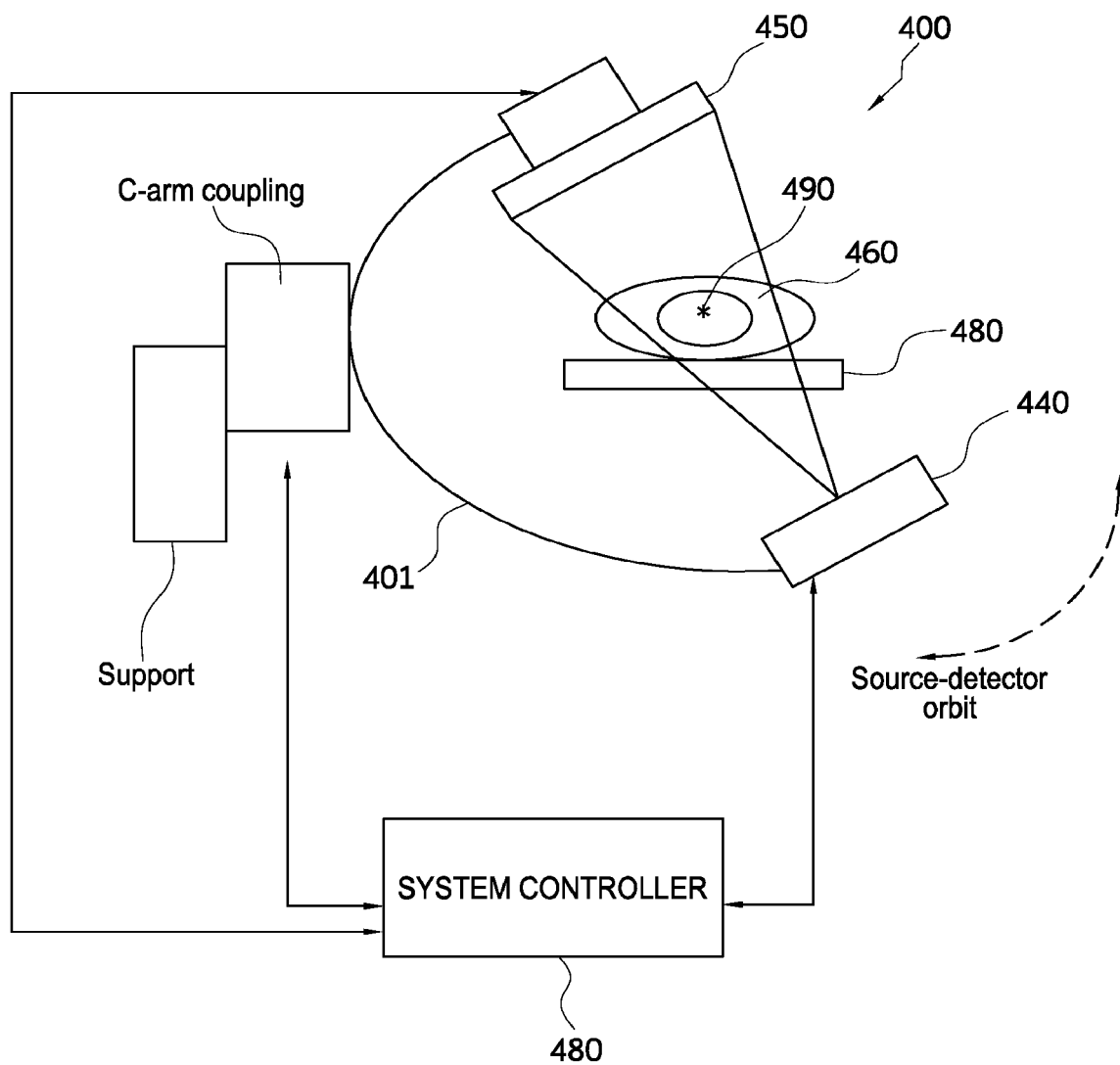
FIG. 4 is a perspective view of an imaging system employing a cone-beam computed tomographic image acquisition mode, according to one or more embodiments of the disclosed subject matter.
Figure 5A:
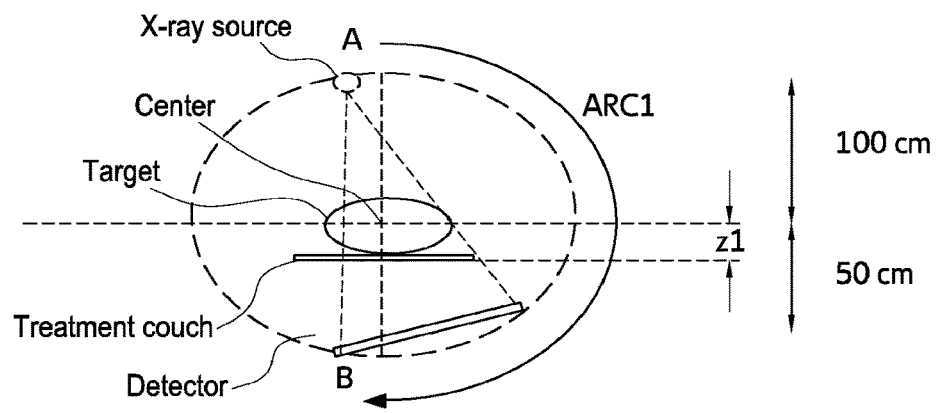
FIG. 5 illustrates a conventional image scan trajectory of 180+fan angle scan.
Figure 5B:
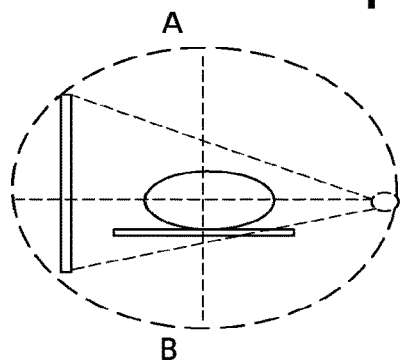
Figure 5C:
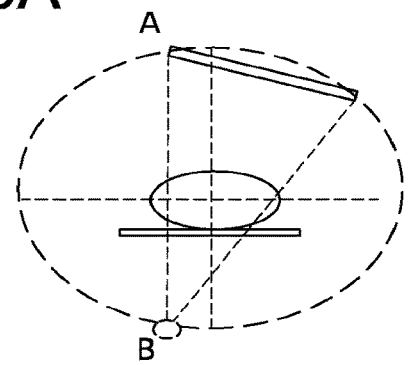
Figure 6:
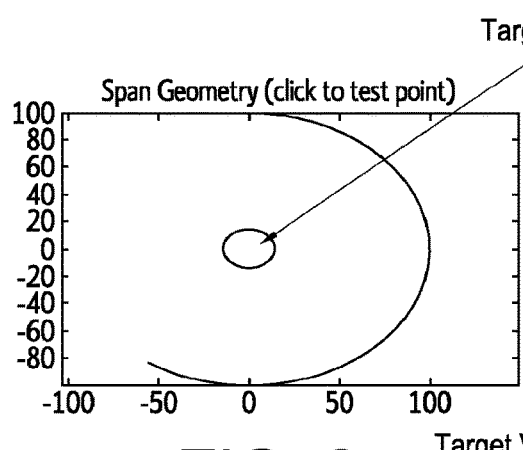
FIG. 6 illustrates a scanning diameter of a target volume obtained for the scan trajectory shown in FIG. 5.
Figure 7:
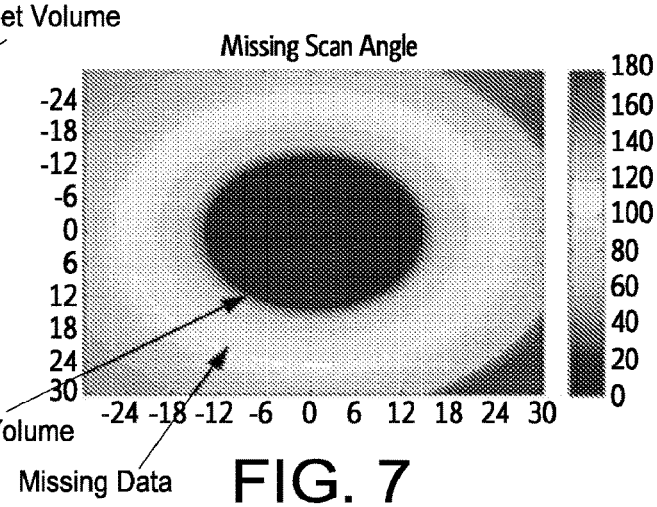
FIG. 7 illustrates a central slice of a reconstructed volume obtained using the scan trajectory of FIG. 5.

In an alternative embodiment, the system is a C-arm based flat-panel cone-beam computer tomography system 400 as shown in FIG. 4, where a centrally positioned flat-panel imager 450 is attached to a movable isocentric C-arm gantry 401, with the target 460 positioned on a movable treatment couch 480 in between the X-ray source 440 and the flat-panel imager 450.

Imaging is provided by the flat-panel imager 450 that can be fixably mounted to the C-arm 401 to be rotatable in unison with the X-ray source 440 around the patient. The X-ray source 440 is a megavoltage (MV) radiation source, generally in the 4-25 MV energy range and having a field size on the order of between 25 cm and 40 cm maximum, or a kilovoltage (kV) radiation source having a field size which is smaller than 50 cm, for example. The kV source can be a pulsed or a continuous kV source. The X-ray source can selectively apply X-rays to a target volume 460 of a patient positioned on the treatment couch 470. The source 440 applies radiation under the control of a system controller 480. The system controller 480 can comprise a processing circuitry, a detector controller, a couch position controller, and a radiation source controller, each programmed and configured to achieve one or more of the functionalities described herein. The system controller 480 may include the components as described in detail above with regards to the system controller 1000.

The radiation source 440 can selectively emit X-ray imaging radiation under the control of the radiation controller 480, and the imaging radiation that has propagated from the MV source through the target volume 460 can be captured by the flat-panel imager 450. A couch position controller can be used to position the treatment couch 470. The treatment couch 470 can be moved in lateral (along the X-axis), horizontal (along the Y-axis), and vertical planes (along the Z-axis). The treatment couch can be a six-degrees-of-freedom (6DoF) treatment couch, for example. The treatment couch 470 may be connected to the rotatable C-arm 410 via a communications network and is capable of translating in multiple planes along the X, Y and Z axis, and angulation for positioning and repositioning the patient and the target volume 460. The treatment couch 470 can be translated in the horizontal (i.e., along the Y axis), vertical (i.e., along the Z axis) and lateral (i.e., along the X axis) planes, and be coupled to an automated patient positioning system capable of manipulating the patient with three or more degrees of freedom (e.g., three orthogonal translations plus one or more rotations). The three orthogonal translations can include one parallel to the rotation axis (i.e., along the Y axis), and two orthogonal to the rotation axis (i.e., along the X and Z axis).

The C-arm 401 can rotate about the isocenter line (isocenter line extends along the X-axis) to place the radiation source 440 and imager 450 at any position within 360 degrees around the target volume 490 to generate CT scan image data.

The radiation source 440 can emit a divergent beam of megavoltage X-rays along a beam axis. The beam is emitted toward the isocenter 490. Due to the divergence of the beam and the shaping of the beam by beam-shaping devices (not shown), the beam delivers the radiation to a volume 460 of object rather than only to the isocenter 490. The flat panel imager 450 is configured to receive the X-rays that passed through the target volume 460 and to generate images based on the received X-rays. The CBCT scan image data can then be used to generate a three-dimensional representation of the patient anatomy and the target volume 460. The image data may be further used to generate a treatment plan to tailor a dose of therapeutic radiation to the target volume 460.

To control the quality of the images, two types of filters, namely, full and half Bow-tie filters can be added. The main function of the filters is to reduce skin dose, reduce X-ray scatter, which results in improved image quality, reduce the amount of charge trapped in the detector, and to allow higher magnitude X-ray techniques to be used without saturating the detector.

The detector/imager 450 can include a large flat-panel imager, such as an amorphous silicon (a-Si) imager, having up to 43 cm in lateral dimension and ~30-43 cm in longitudinal dimension, for example. Any other detectors and imagers can be used. The imager 450 may be coupled to signal processing circuitry comprising a preamplifier stage to improve contrast resolution and dynamic range.

The C-arm 401 is configured such that the X-ray source 440 and the imager 450 are rotatable around the longitudinally oriented central axis passing through the isocenter 490. Any mechanism, as would be apparent to one of ordinary skill in this art, can be used to achieve such a rotating functionality, including a mechanism in which the C-arm 401 rotates and the source 440 and imager 450 are affixed to the C-arm to rotate around the patient in unison.

The cone-beam scanning procedure includes a repeated sequence of radiographic exposure, array readout, object, and/or radiation source 440 movement as disclosed in detail below. The timing of this scanning procedure is driven by the frame clock of the Image acquisition system which is reading out the imager 450. Projection image acquisition is done by moving the treatment couch 470 laterally (along the X-axis) and/or vertically (along the Z-axis), and/or rotating the C-arm 401 around the target volume 460 and moving the treatment couch 470 laterally and/or vertically. The rotation of the C-arm 401 causes the X-ray source 440 and the flat-panel imager 450 to rotate together around the isocenter 490, such that the isocenter 490 remains located between the X-ray source 440 and the flat-panel imager 450 during rotation. Moving the treatment couch 470 laterally, and/or vertically, and/or horizontally, or in a combination of lateral/vertical/horizontal movements, moves the target volume from a first position to different positions which are shifted relative to the original position. This movement of the target volume leads to a virtual movement of the rotation center relative to the target volume and an increase in the covered scan diameter and thus the imaging volume, as shown in FIGS. 11A-11C, 14A-14C, and 17A-17C, discussed in detail below.

The captured cone-beam CT image projection data may be delivered to a system controller 480 such as the system controller 1000, or be delivered and stored to another computer that can be connected to the command processor module via a communication network. The cone-beam CT image projection data may also be transferred to a cone-beam CT reconstruction computer that includes software designed to achieve rapid cone-beam CT image generation. The computer can merge or reconstruct the image data into a three-dimensional representation of the patient and target volume.

In an embodiment, cone-beam CT reconstruction software can allow for full-cone and partial-cone input data that can produce cone-beam CT images at a specific source-to-imager distance. The cone-beam reconstruction software may also transform the cone-beam CT projection data into volumetric CT image data. The volumetric CT image data may include full-fan and/or partial cone image data to reconstruct head size and body size volumes.

Beam shaping may also be employed along with intensity modulation by directing the X-ray beam through a dynamic multileaf collimator. The multileaf collimator may include a series of metal shims having a center of shim pairs where each shim of the pairs may be individually moved to create a shaped opening capable of shaping the beam. To be effective, the radiation field should be large enough to radiate the entire tumor while at the same time minimize radiating healthy tissue. The multileaf collimator may have shims on one level and in one direction or shims may be stacked in multiple levels where a second stack may have its shims oriented in the same direction as the first stack or oriented principally orthogonally to the first stack. The collimator may be dynamic in that the shims can rapidly move to reshape the beam, which results in blocking the therapeutic beam from striking certain areas of the target volume based on the treatment plan. This results in different areas of the tumor receiving different amounts of radiation over the time that a radiation dose is applied.

The C-arm structure 401 can also be configured to be coupled to and/or integrated with a computer system using one or more busses, networks, or other communication systems including wired or wireless communication systems to implement the imaging and reconstruction methods described herein. Methods of the cone-beam computer tomographic system may be implemented in machine readable code (i.e., software or computer program product) and performed on computer systems.

System 400 may incorporate less or more elements that those shown. In addition embodiments are not limited to the devices shown in these figures.

The image acquisition trajectories/modes used to generate image projections using this system is described in detail below under the heading "Image Acquisition Modes."

B. Image Acquisition Modes

The image acquisition trajectories/modes described below apply for any of the CBCT imaging system platforms described above, and for any other applicable imaging systems with a fixed centrally located detector, where the detector is placed orthogonal to the central beam at a fixed distance from the X-ray source (i.e., SID 150 cm, for example).

In various embodiments, methods of increasing a scanning diameter of an imaging volume are described comprising exposing a scanning object to a plurality of scanning segments (partial scans) using an X-ray source, and moving the scanning object to a different location along a first and/or a second axis orthogonal to a rotation axis of the X-rays source for each scanning segment (partial scan).

In various embodiments the plurality of scanning segments includes two 180 degree+fan angle scanning segments.

In various embodiments, the plurality of scanning segments includes more than two scanning segments, each of the scanning segments partially overlapping a preceding scanning segment. For more than three scanning segments, the partial overlap can be less than the fan angle.

In various embodiments, the method for increasing a scanning diameter of an imaging volume comprises: moving an imaging volume from a first position to a second position along one or more planes which are orthogonal to a rotation axis of an X-ray source, and acquiring a plurality of projection images of the imaging volume positioned at the first position and at the second position by moving the X-ray source around an arc segment and irradiating the imaging volume with X-rays.

In various embodiments, the method for increasing an imaging volume comprises: acquiring a plurality of projection images of an imaging volume by moving an X-rays source around the imaging volume and irradiating the imaging volume with X-rays, wherein the plurality of projection images are associated with a plurality of locations of the imaging volume along one or more planes which are orthogonal to the rotation axis of the X-ray source.

In various embodiments, an image acquisition process includes the steps of: acquiring a plurality of sets of projection images using an X-ray source, each of the plurality of sets of projection images being associated with a respective one of a plurality of locations of the X-ray source along a scanning arc segment, and a respective one of a plurality of locations of the treatment couch along planes that are orthogonal to the rotation axis of the X-rays source (e.g., rotation axis of the gantry), and generating a three-dimensional image of the volume based on the plurality of projection image sets.

1. Two Short Lateral Scans (Double Short Scan)

Figure 8:
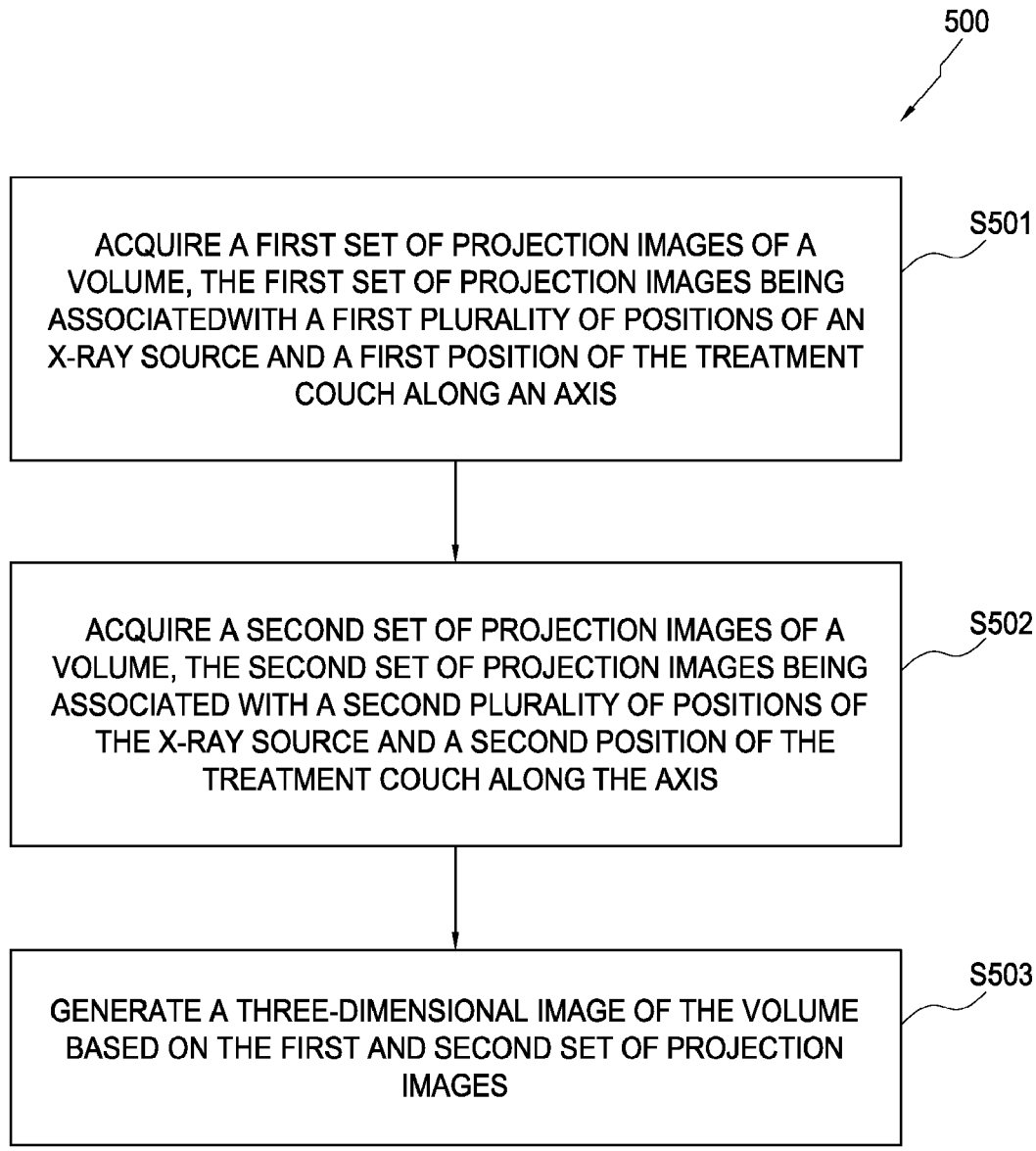
FIG. 8 illustrates a flow diagram of an image acquisition process, according to one or more embodiments of the disclosed subject matter.

FIG. 8 is a flow diagram of a process 500 according to some embodiments. Process 500 and the other processes described herein may be performed using any suitable combination of hardware and software or manual means and may be performed using any of the above described systems (100, 300, 400) or any other imaging systems. Software embodying these processes may be stored by any medium, including a fixed disk, a floppy disk, a CD-ROM, a DVD-ROM, a Zip disk, a magnetic tape, or a signal.

Process 500 may be performed at any time, including during positioning or during a radiation treatment fraction. In some embodiments, and prior to step S501, an operator may manipulate the input device of an operator console to initiate operation of the system 100, 300, or 400, to execute a radiation treatment plan. In response, the system controller 1000, 308, 408 may execute a program code of a system control application stored in storage. The operator may then operate the input device to initiate a patient positioning procedure, for example, requiring a three-dimensional image of a patient volume.

At S501, a first set of projection images of a volume is acquired using an X-ray source. The X-ray source could be a MV or a kV X-ray source. The first set of projection images includes a first plurality of projection images, each of the first plurality of projection images being associated with a respective one of a first plurality of X-ray source positions along a first scanning segment and a first location of the treatment couch.

At S502, a second set of projection images of a volume is acquired using the X-ray source. The second set of projection images includes a second plurality of projection images, each of the second plurality of projection images being associated with a respective one of a second plurality of X-ray source positions along a second scanning segment and a second location of the treatment couch.

At S503, volume reconstruction is performed to generate a three-dimensional image of the target volume based on the first set of projection images and the second set of projection images. Various reconstruction algorithms have been developed, which include filtered back-projection and iterative reconstruction algorithms, described in detail below, to reconstruct the images at step S503.

FIGS. 9A-9E illustrate a scanning trajectory to obtain step S501.

Figure 9A:
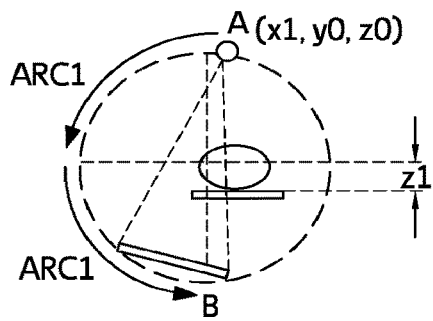
FIGS. 9A-10E illustrate an image acquisition process according to one or more embodiments of the disclosed subject matter.
Figure 9B:
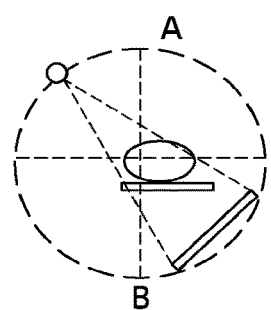
Figure 9C:
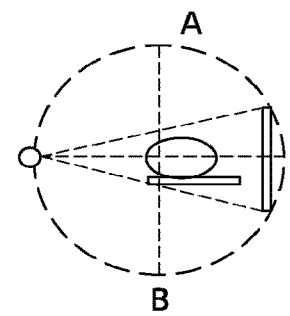
Figure 9D:
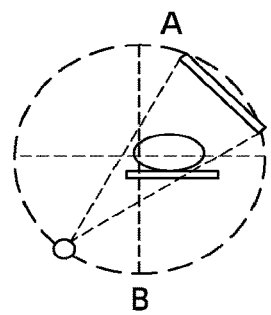
Figure 9E:
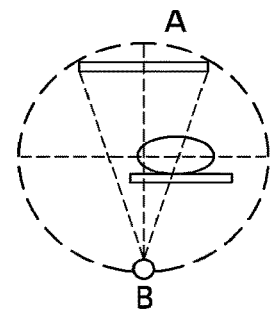

FIG. 9A illustrates the position of the source, detector/imager, and treatment couch in respective first positions prior to step S501. In this position, the X-ray source is located at position A and the centrally located detector/imager is located across from the source. The patient is positioned on a treatment couch so that the center (Center$_1$) of the target volume is located at a first position ($x_1$, $y_0$, $z_0$), which is shifted from its central location ($x_0$, $y_0$, $z_0$) along the X axis. Thus, prior to step S501, the treatment couch is laterally moved by a distance $d_1$, which could be, but is not limited to, approximately 8 cm from its central location, so as to position the target volume from its original central position ($x_0$, $y_0$, $z_0$), to the first position ($x_1$, $y_0$, $z_0$).

FIGS. 9B-9E illustrate the movement of the X-ray source around the target volume from a first position A to a second position B, and the scanning trajectory along a first arc segment ARC1. In one illustrative embodiment, the first arc segment encompasses approximately 180 degrees. A first set of projection images are acquired during the movement of the X-rays source along the first arc segment ARC1 while the target volume is located at a first position along the X-axis.

FIGS. 10A-10E illustrate a scanning trajectory to obtain step S502.

Figure 10A:
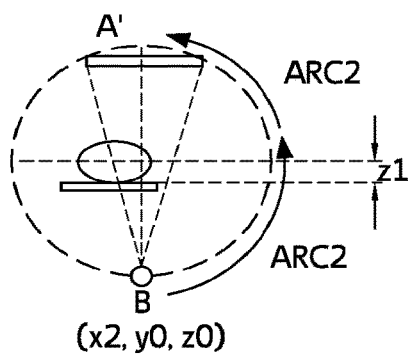
Figure 10B:
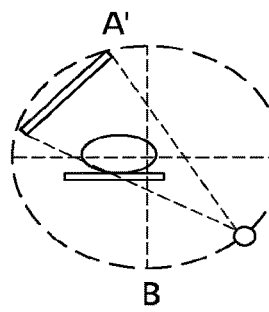
Figure 10C:
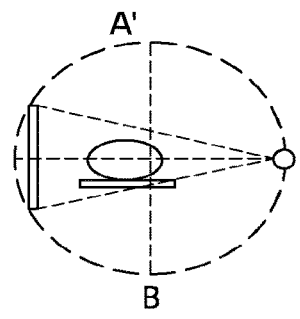
Figure 10D:
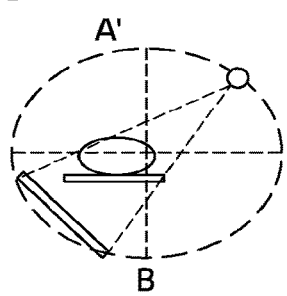
Figure 10E:
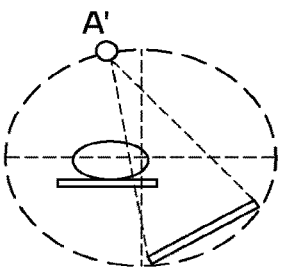

FIG. 10A illustrates the position of the source, detector/imager, and treatment couch in respective positions prior to step S502. In this position, the X-ray source is located at position B and the centrally located detector/imager is located across from the source. The patient is positioned on a treatment couch so that the center (Center$_2$) of the target volume is located at a second position ($x_2$, $y_0$, $z_0$), which is shifted from its central location ($x_0$, $y_0$, $z_0$) along the X axis. Thus, after the end of step S501 and prior to step S502, the treatment couch is laterally moved by a distance $d_2$, which could be, but is not limited to, approximately 8 cm from its central location, so as to position the target volume from the first position ($x_1$, $y_0$, $z_0$) to a second position ($x_2$, $y_0$, $z_0$).

FIGS. 10B-10E illustrate the movement of the X-ray source around the target volume from position B to position A' around scanning arc segment ARC2. In one embodiment, the second arc segment ARC2 encompasses 180 degrees+ fan angle. A second set of projection images are acquired during the movement of the X-rays source along the second arc segment ARC2 while the target volume is located at the second position along the X-axis. Because for a full CBCT data reconstruction at least 180 degree rotation+fan angle is needed, the size of the overlap between the two arc segments can have a size which is substantially the size of the fan angle.

In the illustrative embodiment, projection images are not acquired during the movement of the treatment couch from the original/central to the first and from the first to the second couch positions. Instead, the first set of projection images are acquired after the treatment couch is positioned at the first location, and the second projection images are acquired after the treatment couch is positioned at its second position. However, in an alternative embodiment, the first set of projection images can be acquired by moving the X-ray source along the first scanning arc segment ARC1 while the treatment couch is moved continuously from its original position to its first position, and the second set of projection images can be acquired by moving the X-ray source along the second scanning arc segment ARC2 while the treatment couch is moved continuously from the first position to the second position.

In the illustrative embodiment, projection images are not acquired during the movement of the treatment couch from the original to the first couch position and from the first to the second couch position. However, in an alternative embodiment, additional projection images may be taken during the movement of the treatment couch from the original to the first, and/or from the first to the second couch positions.

This combined scanning trajectory, namely, the scanned ARC1 segment with the couch at the first position and scanned ARC2 segment with the couch at the second position, provides a larger sampling of the target volume than provided by conventional circular CBCT systems, because, as illustrated in FIGS. 11A-11B, the obtained target volume is a combination of the imaging volume obtained during the first scanning trajectory along arc segment ARC1 and the imaging volume obtained during the second scanning trajectory along arc segment ARC2. FIG. 11C shows the reconstruction diameter obtained for such a scanning trajectory.

At step S503 reconstruction can be performed to generate a three-dimensional image of the volume based on the first set of projection images and the second set of projection images. Various digital tomosynthesis, CT, and CBCT reconstruction algorithms have been developed, which include filtered back-projection and iterative reconstruction algorithms, described in detail below, to reconstruct the images at step S503. The reconstructed three-dimensional image of the target volume can be displayed or stored and used in various applications such as matching, segmentation, planning, review, etc.

2. Two Short Lateral Scans and a Third Vertical Scan

Figure 12:
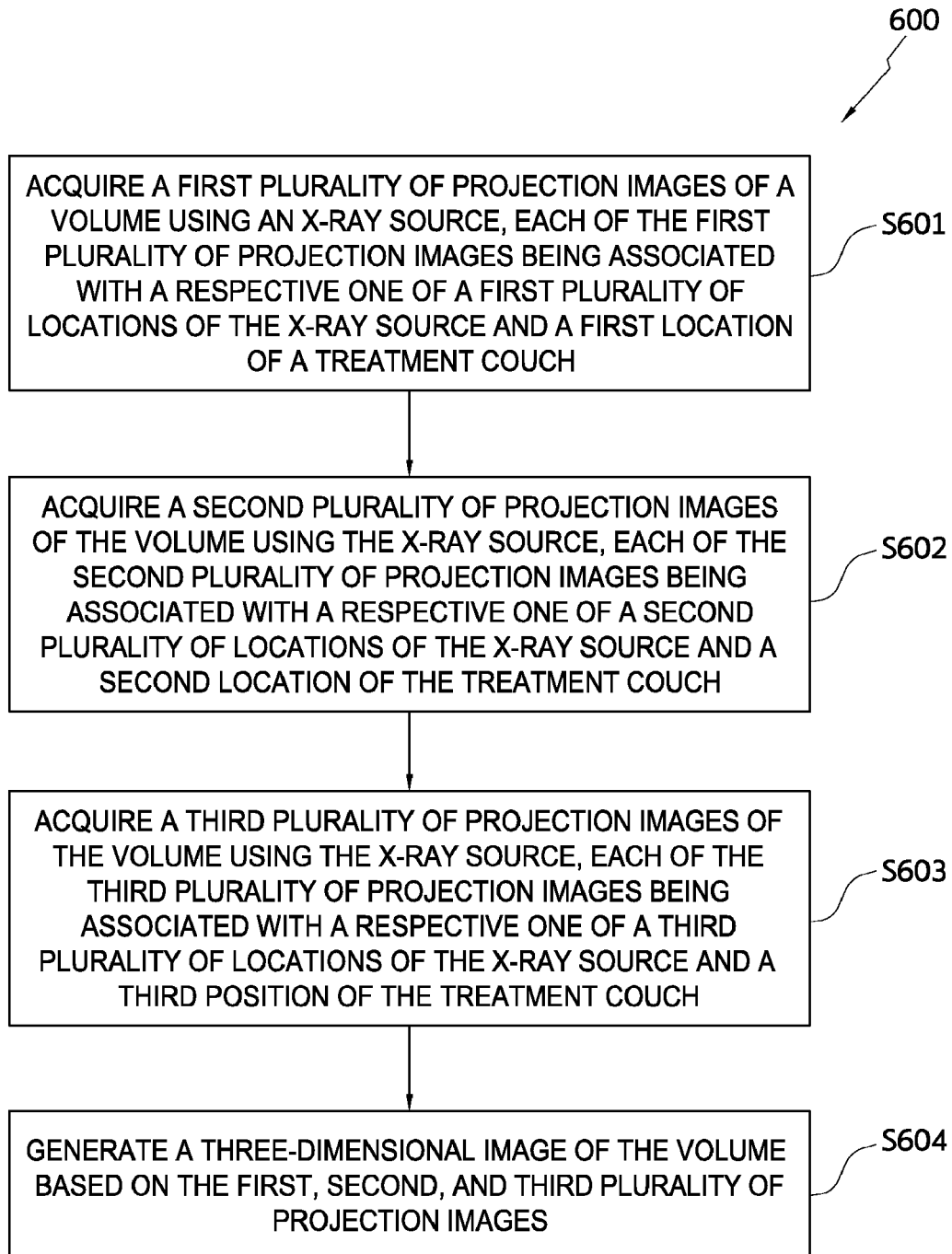
FIG. 12 illustrates a flow diagram of an image acquisition process, according to one or more embodiments of the disclosed subject matter.

FIG. 12 is a flow diagram of a process 600 according to some embodiments.

Process 600 and the other processes described herein may be performed using any suitable combination of hardware and software or manual means and may be performed using any of the above described systems (100, 300, 400) or any other imaging systems. Software embodying these processes may be stored by any medium, including a fixed disk, a floppy disk, a CD-ROM, a DVD-ROM, a Zip disk, a magnetic tape, or a signal.

Process 600 may be performed at any time, including during patient positioning or during a radiation treatment fraction. In some embodiments, and prior to step S601, an operator may manipulate the input device of an operator console to initiate operation of the system 100, 300, or 400, to execute a radiation treatment plan. In response, the system controller 1000, 308, 408 may execute a program code of a system control application stored in storage. The operator may then operate the input device to initiate a patient positioning procedure, for example, requiring a three-dimensional image of a patient volume.

At S601, a first set of projection images of a volume is acquired using an X-ray source. The X-ray source could be a MV or a kV X-ray source. The first set of projection images includes a first plurality of projection images, each of the first plurality of projection images being associated with a respective one of a first plurality of X-ray source positions along a first scanning segment and a first location of the treatment couch.

At S602, a second set of projection images of a volume is acquired using the X-ray source. The second set of projection images includes a second plurality of projection images, each of the second plurality of projection images being associated with a respective one of a second plurality of X-ray source positions along a second scanning segment and a second location of the treatment couch.

At S603, a third set of projection images of a volume is acquired using the X-ray source. The third set of projection images is associated with a third plurality of projection images, each of the third plurality of projection images being associated with a respective one of a third plurality of X-ray source positions along a third scanning segment and a third location of the treatment couch.

At S604, volume reconstruction is performed to generate a three-dimensional image of the target volume based on the first, second, and third sets of projections. Various reconstruction algorithms have been developed, which include filtered back-projection and iterative reconstruction algorithms, described in detail below, to reconstruct the images at step S604.

FIGS. 13A-13E illustrate a scanning trajectory to obtain step S601.

FIG. 13A illustrates the position of the source, detector/imager, and treatment couch in respective first positions prior to step S601. In this position, the X-ray source is located at position A and the centrally located detector/imager is located across from the source. The patient is positioned on a treatment couch so that the center (Center$_1$) of the target volume is located at a first position $(x_1, y_0, z_0)$, which is shifted from its central location $(x_0, y_0, z_0)$ along the X axis. Thus, prior to step S601, the treatment couch is laterally moved by a distance $d_1$, which could be, but is not limited to, approximately 8 cm from its central location, so as to position the target volume from its central position $(x_0, y_0, z_0)$, to the first position $(x_1, y_0, z_0)$.

FIGS. 13B-13E illustrate the movement of the X-ray source around the target volume from a first position A to a second position B, and the scanning trajectory along a first arc segment ARC1. In one illustrative embodiment, the first arc segment encompasses approximately 120 degrees. A first set of projection images are acquired during the movement of the X-rays source along the first arc segment ARC1 while the target volume is located at a first position along the X-axis.

FIGS. 13'A-13'E illustrate a scanning trajectory to obtain step S602.

FIG. 13'A illustrates the position of the source, detector/imager, and treatment couch in respective positions prior to step S602. In this position, the X-ray source is located at position B' and the centrally located detector/imager is located across from the source. The patient is positioned on a treatment couch so that the center (Center$_2$) of the target volume is located at a second position $(x_2, y_0, z_0)$, which is shifted from its central location $(x_0, y_0, z_0)$ along the X axis. Thus, after step S601 and prior to step S602, the treatment couch is laterally moved by a distance $d_2$, which could be, but is not limited to, approximately 8 cm from its central location, so as to position the target volume from the first position $(x_1, y_0, z_0)$, to a second position $(x_2, y_0, z_0)$. During the movement of the treatment couch from the first position to the second position, the gantry is rotated so that the X-ray source is moved to position B'.

FIGS. 13'B-13'E illustrate the movement of the X-ray source around the target volume from position B' to position A' around scanning arc segment ARC2. In one embodiment, the second arc segment encompasses approximately 120 degrees. A second set of projection images are acquired during the movement of the X-rays source along the second arc segment ARC2 while the target volume is located at the second position along the X-axis.

Figure 13F:
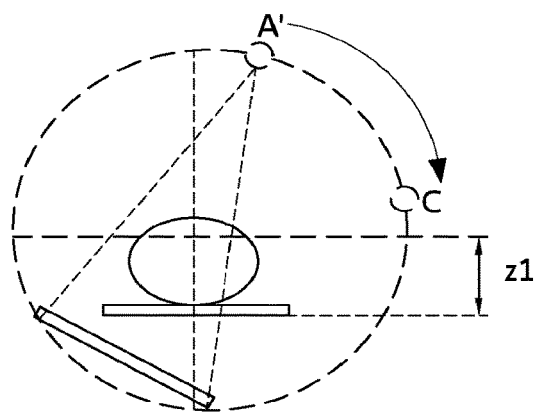
Figure 13G:
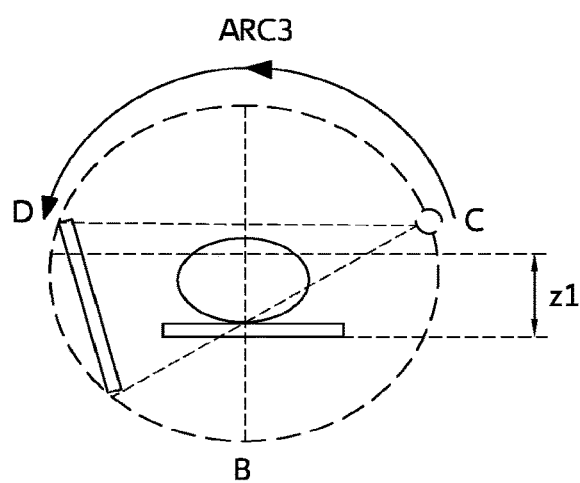
Figure 13H:
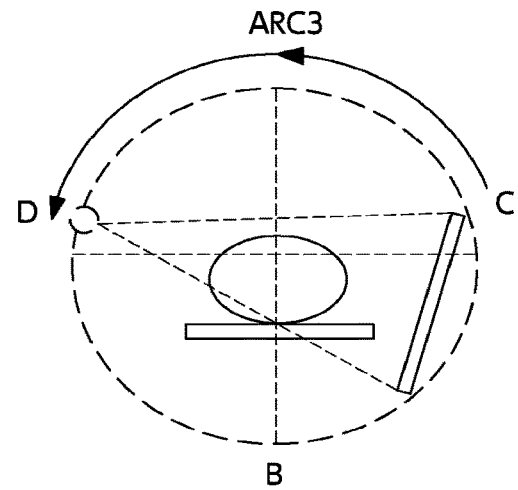

FIGS. 13F-13H illustrate a scanning trajectory to obtain step S603.

FIG. 13F illustrates the positions of the source, detector/imager, and treatment couch prior to step S603. In this position, the X-ray source is located at position A' and the centrally located detector/imager is located across from the source. The patient is positioned on a treatment couch so that the center (Center$_3$) of the target volume is located at a third position $(x_0, y_0, z_1)$, which is shifted from its central location $(x_0, y_0, z_0)$ along the Z axis. Thus, prior to step S603, the treatment couch is moved to the center position along the X-axis, and lowered by a distance $d_3$, which could be, but is not limited to, approximately 8 cm from its central location along the vertical axis Z, so that the center (Center$_3$) of the target volume is located at a third position $(x_0, y_0, z_1)$. While the treatment couch is being moved to its third position, the gantry is rotated so that the X-ray source is moved to a position C.

FIG. 13G illustrates the movement of the X-ray source around the target volume from position C to position D around a third scanning arc segment ARC3. In one illustrative embodiment, the third arc segment ARC3 encompasses approximately 120 degrees plus the overlap between the first, second, and third arc segments. A third set of projection images are acquired during the movement of the X-rays source along the third arc segment ARC3 while the target volume is located at the third position. For a full CBCT data reconstruction, the overlap can be smaller than the fan angle.

In the illustrative embodiment, projection images are not acquired during the movement of the treatment couch from the original to the first, from the first to the second, and from the second to the third couch positions. Instead, the first set of projection images are acquired after the treatment couch is positioned at the first location, the second projection images are acquired after the treatment couch is positioned at its second position, and the third set of projection images are acquired after the treatment couch is positioned at its third position. However, in an alternative embodiment, additional projection images may be taken during the movement of the treatment couch from the original to the first, and/or from the first to the second, and/or from the second to the third couch positions.

Also, in the illustrative embodiment, the first scanning segment ARC1 encompasses about 120 degrees, the second scanning segment ARC2 encompasses about 120 degrees, and the third scanning segment ARC3 encompasses 120 degrees and the overlap for a full CT image reconstruction. However, either one, two, or all of the first, second and third scanning segments can encompass more than 120 degrees.

Moreover, additional projection images may also be taken while the X-ray source is being moved from its position at the end of step S602 (i.e., position A') to its position prior to step S603 (i.e., position C).

In yet another alternative embodiment, the first set of projection images can be acquired by moving the X-ray source along the first scanning arc segment ARC1 while the treatment couch is moved continuously from its original position to its first position, the second set of projection images can be acquired by moving the X-ray source along the second scanning arc segment ARC2 while the treatment couch is moved continuously from the first position to the second position, and the third set of projection images can be acquired by moving the X-ray source along the third scanning arc segment ARC3 while the treatment couch is moved continuously from its second to its third location.

This combined scanning trajectory, namely, the scanned ARC1 segment with the couch at the first position, scanned ARC2 segment with the couch at the second position, and scanned ARC3 segment with the couch at the third position provides a larger sampling of the target volume than provided by conventional circular CBCT systems, because, as illustrated in FIGS. 14A-14B, the obtained target volume is a combination of the imaging volume obtained during the first scanning trajectory along arc segment ARC1, the imaging volume obtained during the second scanning trajectory along arc segment ARC2, and the imaging volume obtained during the scanning trajectory along arc segment ARC3. FIG. 14C shows the reconstruction diameter obtained for such a scanning trajectory.

At step S604 digital tomosynthesis or CBCT reconstruction can be performed to generate a three-dimensional image of the volume based on the first, second, and third sets of projection images. Various digital tomosynthesis, CT, and CBCT reconstruction algorithms have been developed, which include filtered back-projection and iterative reconstruction algorithms, described in detail below, to reconstruct the images at step S604. The reconstructed three-dimensional image of the target volume can be displayed or stored and used in various applications such as matching, segmentation, planning, review, etc.

3. Quadratic Scan

Figure 15:
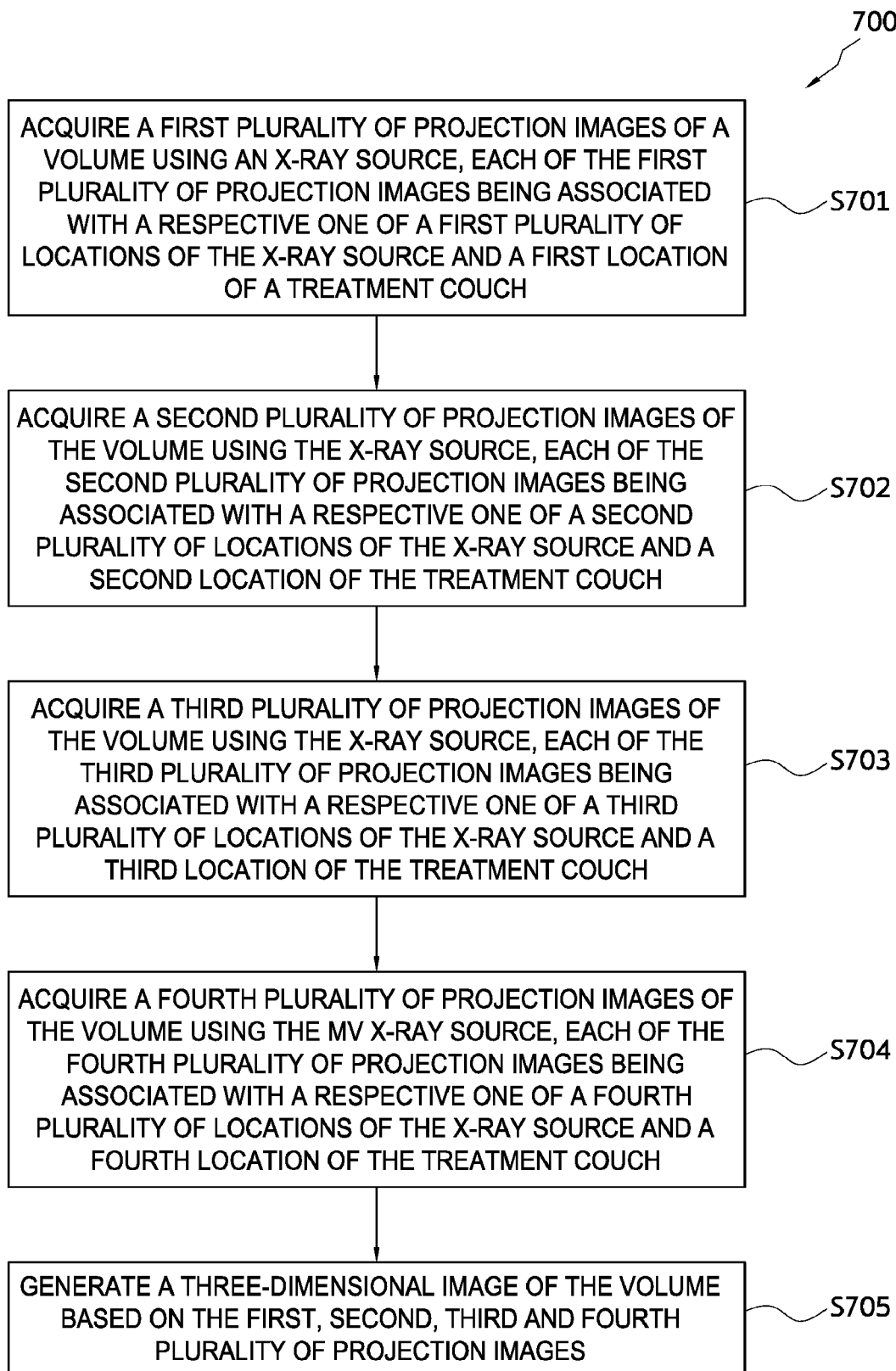
FIG. 15 illustrates a flow diagram of an image acquisition process, according to one or more embodiments of the disclosed subject matter.

FIG. 15 is a flow diagram of a process according to some embodiments. Process 700 and the other processes described herein may be performed using any suitable combination of hardware and software or manual means and may be performed using any of the above described systems (100, 300, 400) or any other imaging systems. Software embodying these processes may be stored by any medium, including a fixed disk, a floppy disk, a CD-ROM, a DVD-ROM, a Zip' disk, a magnetic tape, or a signal.

Process 700 may be performed at any time, including during patient positioning or during a radiation treatment fraction. In some embodiments, and prior to step S701, an operator may manipulate the input device of an operator console to initiate operation of the system 100, 300, or 400, to execute a radiation treatment plan. In response, the system controller 1000, 308, 408 may execute a program code of a system control application stored in storage. The operator may then operate the input device to initiate a patient positioning procedure, for example, requiring a three-dimensional image of a patient volume.

At S701, a first set of projection images of a volume is acquired using an X-ray source. The X-ray source could be a MV or a kV X-ray source. The first set of projection images includes a first plurality of projection images, each of the first plurality of projection images being associated with a respective one of a first plurality of X-ray source positions along a first scanning segment and a first location of the treatment couch.

At S702, a second set of projection images of a volume is acquired using the X-ray source. The second set of projection images includes a second plurality of projection images, each of the second plurality of projection images being associated with a respective one of a second plurality of X-ray source positions along a second scanning segment and a second location of the treatment couch.

At S703, a third set of projection images of a volume is acquired using the X-ray source. The third set of projection images includes a third plurality of projection images, each of the third plurality of projection images being associated with a respective one of a third plurality of X-ray source positions along a third scanning segment and a third location of the treatment couch.

At S704, a fourth set of projection images of a volume is acquired using the X-ray source. The fourth set of projection images includes a fourth plurality of projection images, each of the fourth plurality of projection images being associated with a respective one of a fourth plurality of X-ray source positions along a fourth scanning segment and a fourth location of the treatment couch.

FIGS. 16A-16D illustrate embodiments to obtain steps S701, S702, 703, and S704.

Figure 16A:
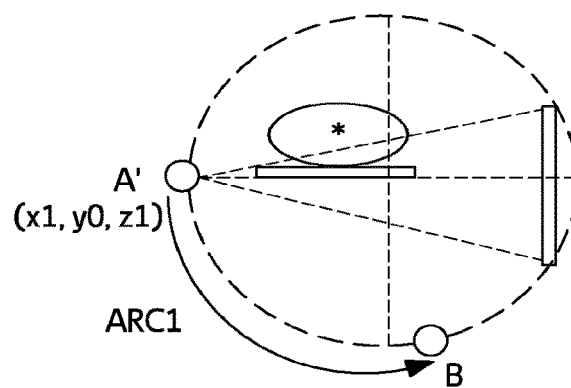
FIGS. 16A-16C illustrate an image acquisition mode according to one or more embodiments of the disclosed subject matter.

FIG. 16A illustrate illustrates the positions of the source, detector/imager, and treatment couch prior to step S701, and the scanning trajectory to obtain step S701. The X-ray source is located at position A' and the centrally located detector/imager is located across from the source. The treatment couch with the patient is moved laterally along the X-axis and vertically along the Z-axis, from its original position to a first position so that the center (Center$_1$) of the target volume is located at a first position ($x_1$, $y_0$, $z_1$), which is shifted from its central location ($x_0$, $y_0$, $z_0$) along the X and Z axis. Thus, prior to step S701, the treatment couch is laterally moved by a distance $d_1$, which could be, but is not limited to, approximately 8 cm from its central location, and vertically moved by a distance $d_2$ so as to position the target volume from its original central position ($x_0$, $y_0$, $z_0$), to the first position ($x_1$, $y_0$, $z_1$).

FIG. 16A also illustrate the movement of the X-ray source around the target volume from a first position A' to a second position B, and the scanning trajectory along a first arc segment ARC1. In one illustrative embodiment, the first arc segment encompasses approximately 90 degrees plus some scan overlap. A first set of projection images are acquired during the movement of the X-rays source along the first arc segment ARC1 while the target volume is located at the first position.

Figure 16B:
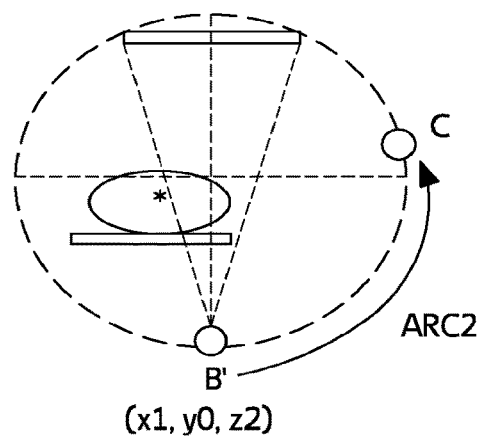

FIG. 16B illustrates the positions of the source, detector/imager, and treatment couch prior to step S702 and the scanning trajectory to obtain step S702. The X-ray source is located at position B' and the centrally located detector/imager is located across from the source. The patient is positioned on a treatment couch so that the center (Center$_2$) of the target volume is located at a second position ($x_1$, $y_0$, $z_2$), which is shifted from its central location ($x_0$, $y_0$, $z_0$) along the X and Z-axis. Thus, prior to step S702, the treatment couch is moved vertically by a distance $d_2$, which could be, but is not limited to, approximately 8 cm from its central location along the Z-axis, so as to position the target volume from its first position ($x_1$, $y_0$, $z_1$) to a second position ($x_1$, $y_0$, $z_2$). While the treatment couch is moved to the second position, the gantry is rotated so as to position the X-ray source from position B where step S701 ended back to a position B'. After the treatment couch is positioned so that the center (Center$_2$) of the target volume is located at a second position ($x_1$, $y_0$, $z_2$), and the X-ray source is at location B', the X-ray source is moved around the target volume from position B' to position C around scanning arc segment ARC2. By moving back the X-ray source to start the second segment scanning at position B', the necessary overlap between the segments is achieved. In one illustrative embodiment, the second arc segment ARC2 encompasses 90 degrees plus some overlap (i.e., overlap between source positions B and B'). A second set of projection images are acquired during the movement of the X-rays source along the second arc segment ARC2 while the target volume is located at the second position.

Figure 16C:
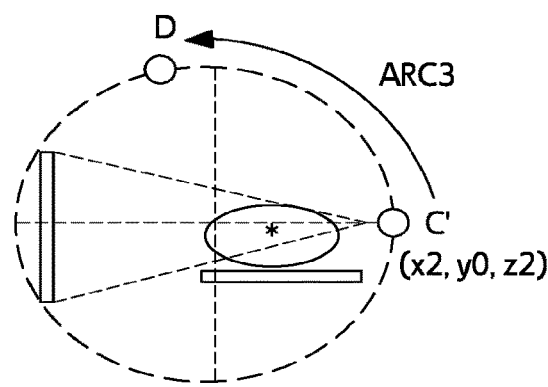

FIG. 16C illustrates the positions of the source, detector/imager, and treatment couch prior to step S703, and a third scanning trajectory to obtain step S703. The X-ray source is located at position C' and the centrally located detector/imager is located across from the source. The treatment couch is moved laterally and vertically so that the center (Center$_3$) of the target volume is located at a third position ($x_2$, $y_0$, $z_2$), which is shifted from its central location ($x_0$, $y_0$, $z_0$) along the X and Z axis. While the treatment couch is moved to its third position, the gantry is rotated so that the X-ray source is moved from position C where step S702 ended to a position C'. After the treatment couch is positioned so that the center (Center$_3$) of the target volume is located at a third position ($x_2$, $y_0$, $z_2$), and the source is at location C', the X-ray source is moved around the target volume from position C' to position D around a third scanning arc segment ARC3. In one illustrative embodiment, the third arc segment ARC3 encompasses 90 degrees plus some overlap (i.e., overlap between source position C and C'). A third set of projection images are acquired during the movement of the X-rays source along the third arc segment ARC3 while the target volume is located at the third position.

Figure 16D:
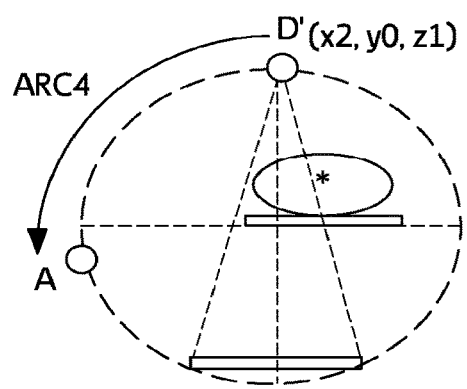

FIG. 16D illustrates the positions of the source, detector/imager, and treatment couch prior to step S704 and a scanning trajectory to obtain step S704. The X-ray source is located at position D' and the centrally located detector/imager is located across from the source. The treatment couch is moved laterally and vertically so that the center (Center$_4$) of the target volume is located at a fourth position ($x_2$, $y_0$, $z_1$), which is shifted from its central location ($x_0$, $y_0$, $z_0$) along the X and Z axis. While the treatment couch is moved to its fourth position, the gantry is rotated so that the X-ray source is moved from position D where step S703 ended to a position D'. After the treatment couch is positioned so that the center (Center$_4$) of the target volume is located at the fourth position ($x_2$, $y_0$, $z_1$), and the source is at location D', the X-ray source is moved around the target volume from position D' to position A around a fourth scanning arc segment ARC4. In one illustrative embodiment, the fourth arc segment ARC4 encompasses 90 degrees plus some overlap (i.e., overlap between source position D and D'). A fourth set of projection images are acquired during the movement of the X-rays source along the fourth arc segment ARC4 while the target volume is located at the fourth position.

In the illustrative embodiment, projection images are not acquired during the movement of the treatment couch from the original to the first, from the first to the second, from the second to the third, and from the third to the fourth couch positions. Instead, the first set of projection images are acquired after the treatment couch is positioned at the first location, the second set of projection images are acquired after the treatment couch is positioned at its second position, the third set of projection images are acquired after the treatment couch is positioned at its third position, and the fourth set of projection images are acquired after the treatment couch is positioned at its fourth position. However, in an alternative embodiment, additional projection images may be taken during the movement of the treatment couch from the first to the second, and/or from the second to the third, and or from the third to the fourth couch positions.

In the illustrative embodiment, the first scanning segment ARC1 encompasses approximately 90 degrees (90 degrees and some overlap), the second scanning segment ARC2 encompasses approximately 90 degrees (90 degrees and some overlap), the third scanning segment ARC3 encompasses approximately 90 degrees (90 degrees and some overlap), and the fourth scanning segment ARC4 approximately 90 degrees (90 degrees and some overlap) for a full CT image reconstruction. However, either one, two, three, or all of the first, second, third, and fourth scanning segments can encompass more than 90 degrees.

Moreover, additional projection images may also be taken while the X-ray source is being moved from its position at the end of step S701 (i.e., position B) to its position prior to step S702 (i.e., position B'), and/or from its position at the end of step S702 (i.e., position C) to its position prior to step S703 (i.e., position C'), and/or from its position at the end of step S703 (i.e., position D) to its position prior to step S704 (i.e., position D').

In yet another alternative embodiment, the first set of projection images can be acquired by moving the X-ray source along the first scanning arc segment ARC1 while the treatment couch is moved continuously from its first to its second position, the second set of projection images can be acquired by moving the X-ray source along the second scanning arc segment ARC2 while the treatment couch is moved continuously from the second to the third position, the third set of projection images can be acquired by moving the X-ray source along the third scanning arc segment ARC3 while the treatment couch is moved continuously from its third to its fourth location, and the fourth set of projection images can be acquired by moving the X-ray source along the fourth scanning arc segment ARC4 while the treatment couch is moved continuously from its fourth location back to its first location.

This combined scanning trajectory, namely, the scanned ARC1 segment with the couch at the first position, scanned ARC2 segment with the couch at the second position, scanned ARC3 segment with the couch at the third position, and scanned ARC4 segment with the couch at the fourth position provides a larger sampling of the target volume than provided by conventional circular CBCT systems, because, as illustrated in FIGS. 17A-17B, the obtained target volume is a combination of the imaging volume obtained during the first scanning trajectory along arc segment ARC1, the imaging volume obtained during the second scanning trajectory along arc segment ARC2, the imaging volume obtained during the scanning trajectory along arc segment ARC3, and the imaging volume obtained during the scanning trajectory along the arc segment ARC4. FIG. 17C shows the reconstruction diameter obtained for such a scanning trajectory.

At step S705 digital tomosynthesis or CBCT reconstruction can be performed to generate a three-dimensional image of the volume based on the first, second, third and fourth sets of projection images. Various digital tomosynthesis and CT reconstruction algorithms have been developed, which include filtered back-projection and iterative reconstruction algorithms, described in detail below, to reconstruct the images at step S705. The reconstructed three-dimensional image of the target volume can be displayed or stored and used in various applications such as matching, segmentation, planning, review, etc.

4. Segment Scan with Lateral and Vertical Movement

Figure 18:
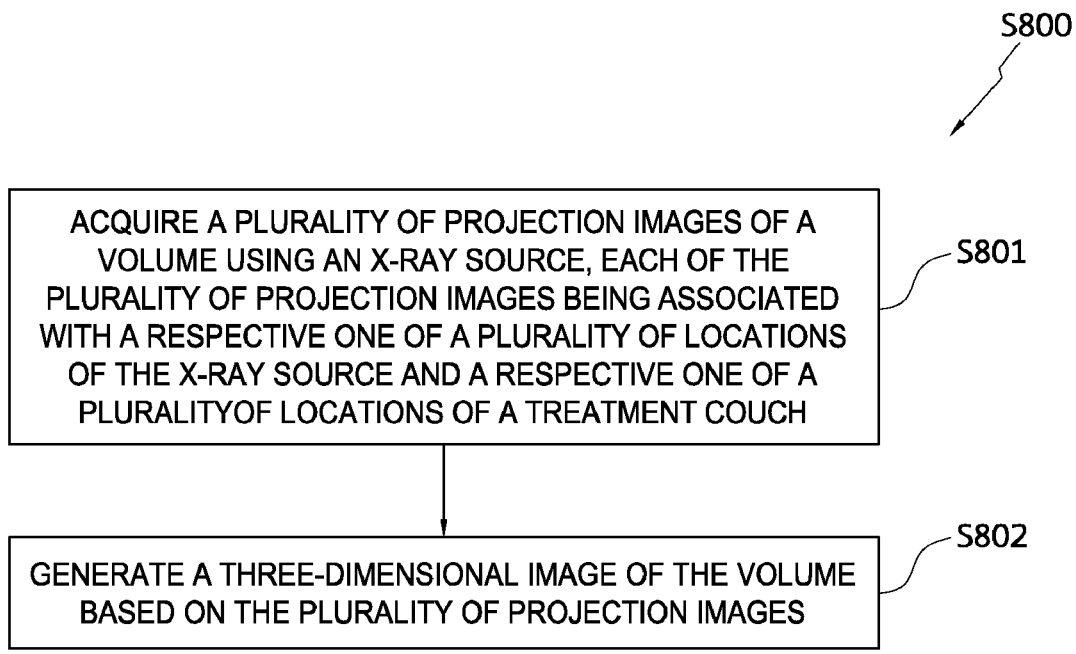
FIG. 18 illustrates a flow diagram of an image acquisition process, according to one or more embodiments of the disclosed subject matter.
Figure 19A:
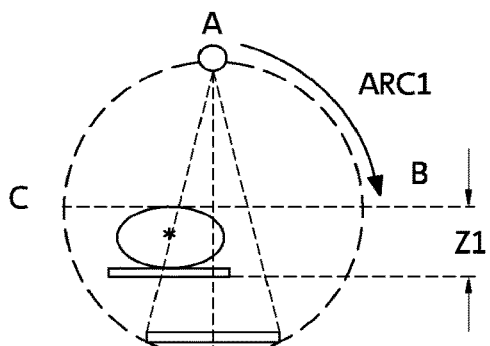
FIGS. 19A-19H illustrate an image acquisition mode according to one or more embodiments of the disclosed subject matter.
Figure 19B:
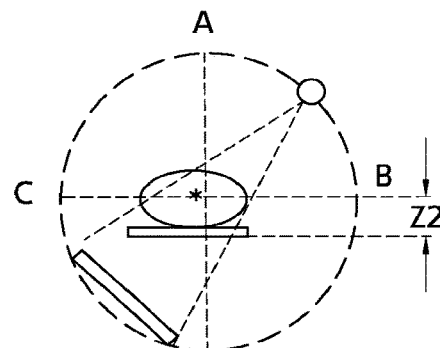
Figure 19C:
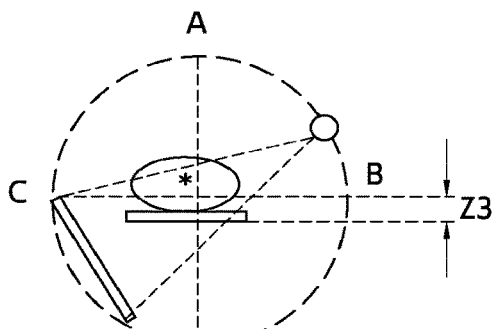
Figure 19D:
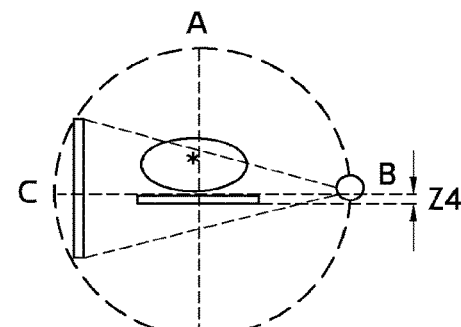
Figure 19E:
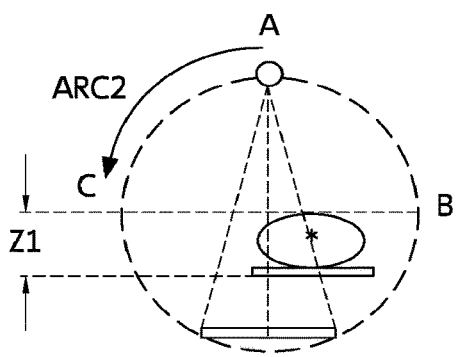
Figure 19F:
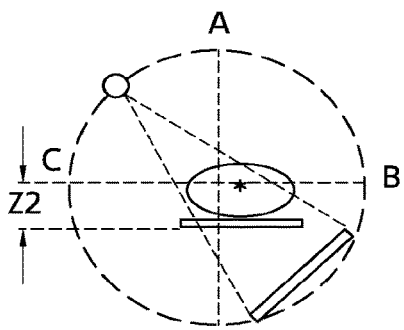
Figure 19G:
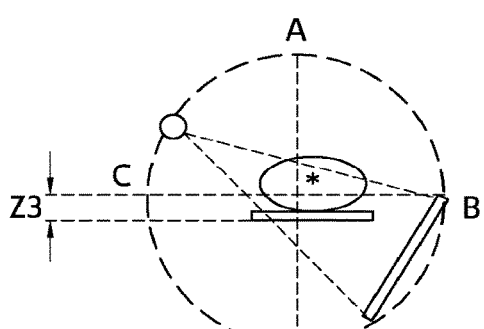
Figure 19H:
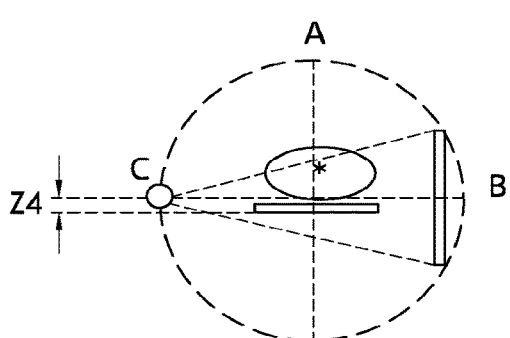

FIG. 18 is a flow diagram of a process according to some embodiments. Process 800 and the other processes described herein may be performed using any suitable combination of hardware and software or manual means and may be performed using any of the above described systems (100, 300, 400) or any other imaging systems. Software embodying these processes may be stored by any medium, including a fixed disk, a floppy disk, a CD-ROM, a DVD-ROM, a Zip disk, a magnetic tape, or a signal.

Process 800 may be performed at any time, including during calibration or during a radiation treatment fraction. In some embodiments, and prior to step S801, an operator may manipulate the input device of an operator console to initiate operation of the system 100, 300, or 400, to execute a radiation treatment plan. In response, the system controller 1000, 308, 408 may execute a program code of a system control application stored in storage. The operator may then operate the input device to initiate a patient positioning procedure, for example, requiring a three-dimensional image of a patient volume.

At S801, a set of projection images are acquired using an X-ray source. The X-ray source could be a MV or a kV X-ray source. The set of projection images includes a plurality of projection images, each of the plurality of projection images being associated with a respective one of a plurality of discrete locations of the X-ray source around an arc segment, and a respective one of a plurality of discrete locations of the treatment couch along a first and a second plane which are orthogonal to the rotation axis of the gantry.

At S802, a three-dimensional image of the volume is generated based on the plurality of projection images acquired.

In embodiments, the plurality of projection images include a plurality of projection images $N_i$ associated with respective ones of a plurality of discrete locations $N_{sourcei}$ of the X-ray source along an arc segment and respective ones of a plurality of discrete locations $N_{couchi}$ of the treatment couch along planes orthogonal to the rotation axis. In embodiments, the arc segment can encompass 180 degrees. In other embodiments, the arc segment can encompass 360 degrees. In yet other embodiments, the arc segment can encompass any arc segment between 180-360 degrees.

In some embodiments the arc segment can include two arc segments, a first arc segment spanning approximately 90 degrees+some overlap and another scan segment spanning approximately 90 degrees+some overlap.

FIG. 19A-19H illustrates an embodiment where the plurality of projection images are acquired by moving the X-ray source from a first position A to a second position B along an arc segment ARC1 spanning approximately 90 degrees, followed by moving the X-ray source from the first position A to a third position C along an arc segment ARC2 spanning approximately 90 degrees. During the first arc segment, projection images are acquired at a plurality (four (4) shown) discrete positions of the X-rays source along the first arc segment, each of the discrete X-ray source positions being associated with a corresponding position of the treatment couch along the X and Z axis. During the second arc segment, projection images are acquired at a plurality (four (4) shown) discrete positions of the X-rays source along the second arc segment, each of the discrete X-ray source positions being associated with a corresponding position of the treatment couch along the X and Z axis.

In one embodiment, projection images are not acquired while the treatment couch is being moved between the different positions. Instead projection images are acquired only after the treatment couch has been positioned at a particular position.

In other embodiments, projection images are acquired continuously while the treatment couch is being moved from one location to another location and the X-ray source is moved from one location to another along the arc segments.

The number of projection images, the number of discrete positions, and the spanning of the arc segment may not be limited to the ones shown in the illustrated embodiments. Embodiments may include any number of projection images taken at any number of discrete positions for the treatment couch, X-ray source, and/or any arc segment.

In yet another alternative embodiment, only one set of plurality of projection images are acquired in order to generate a three-dimensional image of the target volume, where the arc segment can span at least 180+fan angle, 360, or any other degrees between 180+fan angle and 360 degrees, and the treatment couch can be positioned at a plurality of different locations along planes that are orthogonal to the gantry rotation axis.

In yet alternative embodiments, a plurality of projection images can be acquired, the plurality of images being associated with a respective one of a plurality of locations of the X-ray source around an arc segment spanning at least 180 degrees+fan angle, and a respective one of a plurality of locations of the treatment couch along a first axis and a second axis, the first axis being orthogonal to the second axis.

A complete sampling of the target volume can be done using these image scanning trajectories.

At step S802 digital tomosynthesis or CBCT reconstruction is performed to generate a three-dimensional image of the volume based on the first set of projection images and the second set of projection images. Various digital tomosynthesis or CT reconstruction algorithms have been developed, which include filtered back-projection and iterative reconstruction algorithms, described in detail below, to reconstruct the images at step S802 or stored and used in various applications such as matching, segmentation, planning, review, etc.

Although, the image acquisition trajectories/modes described above were applied for imaging systems with a fixed centrally located detector, where the detector is placed orthogonal to the central beam at a fixed distance from the X-ray source (i.e., SID 150 cm, for example), the image acquisition trajectories/modes can also be applied for imaging systems with a fixed imager at an off center position, as well as for imaging systems with a moving imager. In such a system both the treatment couch and the imager can be moved for image acquisition.

C. Volume Reconstruction

Various digital tomosynthesis or CBCT reconstruction algorithms, including filtered backprojection and iterative reconstruction algorithms can be applied to reconstruct the target volume using the projection images acquired using any one or a combination of the above described projection acquisition modes.

Using the filtered backprojection method, the X-rays in the projections are ordered and weighed, and then they are convolved with a tailored filter and backprojected to the 3D array of voxels. This process may include the following steps, for example:

the projections data $p(\xi, \theta)$ is transformed into an axial slice $\mu(x, y, z)$ according to:

$$p(u,v;\theta)=p_0 e-\int_0^{SDD}\mu(x,y,z)dy \qquad \text{(Eq. 1)}$$

then corrected for offset-gain and defects according to:

$$I_{proc}(u, v) = K\frac{Iraw(u, v) - Ioffset(u, v)}{Igain(u, v) - Ioffset(u, v)} \qquad \text{(Eq. 2)}$$

then normalized according to:

$$p_1(u, v; \theta) = \ln\left(\frac{p0}{p(u, v; \theta)}\right) = \int_0^{SDD} \mu(x, y, z)\,dy \quad \text{(Eq. 3)}$$

then, if desired, cosine weighted (using Feldkemp weights, for example) according to:

$$p_2(u, v; \theta) = p_1(u, v; \theta)\left[\frac{SDD}{\sqrt{SDD^2 + u^2 + v^2}}\right] \quad \text{(Eq. 4)}$$

then data redundancy weighted (Parker weights), if desired, according to:

$$p_3(u,v;\theta) = p_2(u,v;\theta)w_3(u;\theta) \quad \text{(Eq. 5)}$$

then filtered using a ramp filter, for example, according to:

$$p_4(u, v; \theta) = FT^{-1}[FT[p_3(u, v; \theta)]|\rho|] = p_3(u, v; \theta) * \left(-\frac{1}{\pi^2 u^2}\right) \quad \text{(Eq. 6)}$$

then, if desired, smoothed using an apodization filter to obtain a voxel (i, j, k), which is then repeated for all voxels (i, j, k) and for all projection angles (θ) to obtain a reconstructed 3D image. The reconstructed image volume may be corrected for rings, shading, streaks, motion, lag, metal, truncation, and/or cone-beam artifacts introduced into the image.

Iterative reconstruction methods can also be used for volumetric reconstruction. In this approach, attenuation values in a three-dimensional space get repeatedly estimated until they match the acquired projections best.

It should be appreciated that the cone-beam volumetric reconstruction software can utilize image projection data at non-uniformly spaced gantry angles. Thus, the data collection does not require a precise gantry speed rotation.

It will be appreciated that the processes, systems, and sections described above can be implemented in hardware, hardware programmed by software, software instruction stored on a non-transitory computer readable medium or a combination of the above. For example, a method for can be implemented using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C #.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized.

Embodiments of the method, system, and computer program product can be implemented in hardware and/or software using any known or later developed systems or structures, devices and/or software by those of ordinary skill in the applicable art from the function description provided herein and with a general basic knowledge of control systems, image processing and classification, optical tomography and/or computer programming arts.

Moreover, embodiments of the disclosed method, system, and computer program product can be implemented in software executed on a programmed general purpose computer, a special purpose computer, a microprocessor, or the like.

Features of the disclosed embodiments may be combined, rearranged, omitted, etc., within the scope of the invention to produce additional embodiments. Furthermore, certain features may sometimes be used to advantage without a corresponding use of other features.

Moreover, any of the described systems, methods, and devices can be used with a kilovoltage (kV) X-ray source. Thus, the projection image as well as the volume reconstruction methods can also be applied for projection images obtained using a kV X-ray source.

It is thus apparent that there is provided in accordance with the present disclosure, cone-beam computer tomography apparatus, methods, and devices for acquiring projection images of a volume. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A method for increasing a scanning diameter of an imaging volume of a target positioned on a treatment couch, comprising:
   moving the target relative to a rotation axis of an X-ray source by moving the treatment couch from a first position to a second position along one or more planes which are orthogonal to the rotation axis of the X-ray source; and
   while the treatment couch is positioned at the first position, acquiring a first plurality of projection images of the imaging volume by moving the X-ray source around the rotation axis and irradiating the imaging volume positioned at the first position with X-rays; and
   while the treatment couch is positioned at the second positon, acquiring a second plurality of projection images of the imaging volume by moving the X-ray source around the rotation axis and irradiating the imaging volume positioned at the second position with X-rays,
   wherein the X-ray source is moved around the rotation axis through an arc segment.

2. The method of claim 1, wherein the arc segment includes a range of angles between 180+fan angle and 360 degrees.

3. The method of claim 2, wherein the arc segment includes a first arc segment and a second arc segment, the X-ray source moving around the first arc segment when the imaging volume is positioned at the first position and the X-ray source moving around the second arc segment when the imaging volume is positioned at the second position.

4. The method of claim 3, wherein each of the first plurality of projection images being associated with a respective one of a first plurality of locations of the X-ray source around the first arc segment and the first position of the imaging volume, and each of the second plurality of projection images being associated with a corresponding one of a second plurality of locations of the X-rays source around the second arc segment and the second position of the imaging volume.

5. The method of claim 4, wherein the first arc segment includes a 180 degree angle and the second arc segment includes a 180 degree+fan angle.

6. The method of claim 4, wherein the acquiring of the first plurality of projection images includes acquiring the first plurality of projection images after the imaging volume is in the first position, and acquiring the second plurality of projection images includes acquiring the second projection images after the imaging volume is in the second position.

7. The method of claim 1, further comprising acquiring projection images while the imaging volume is moved from the first to the second position.

8. The method of claim 1, wherein the one or more planes includes a lateral and a vertical plane.

* * * * *

UNITED STATES PATENT AND TRADEMARK OFFICE
CERTIFICATE OF CORRECTION

PATENT NO. : 11,045,151 B2
APPLICATION NO. : 15/036669
DATED : June 29, 2021
INVENTOR(S) : David Kirk Jensen et al.

Page 1 of 1

It is certified that error appears in the above-identified patent and that said Letters Patent is hereby corrected as shown below:

In the Claims

In Claim 1:
Line 15: "positon" should read --position--.

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*